United States Patent [19]
Cottingham

[11] Patent Number: 5,639,428
[45] Date of Patent: Jun. 17, 1997

[54] METHOD AND APPARATUS FOR FULLY AUTOMATED NUCLEIC ACID AMPLIFICATION, NUCLEIC ACID ASSAY AND IMMUNOASSAY

[75] Inventor: Hugh V. Cottingham, Caldwell, N.J.

[73] Assignee: Becton Dickinson and Company, Franklin Lakes, N.J.

[21] Appl. No.: 277,553

[22] Filed: Jul. 19, 1994

[51] Int. Cl.$^6$ .............. G05D 16/00; B01L 3/00; C12Q 1/68; C12N 15/00
[52] U.S. Cl. .............. 422/112; 422/105; 422/99; 422/197; 435/6; 435/91.1; 435/287.2; 435/7.1; 436/518; 935/85; 935/86; 935/87
[58] Field of Search .............. 435/6, 91.1, 91.2, 435/287, 288, 789.1, 290.1, 290.3, 291, 310, 312, 316; 422/52, 55, 57, 61, 68, 71, 113, 105, 112; 935/85, 86, 87, 88, 111; 436/518, 164, 800, 804, 807, 808; 356/246; 472/58, 65, 68.1, 99, 197, 209, 215, 237

[56] References Cited

U.S. PATENT DOCUMENTS

| | | | |
|---|---|---|---|
| 4,623,519 | 11/1986 | Cornut et al. | 422/72 |
| 4,735,502 | 4/1988 | Kaufmann | 356/246 |
| 4,883,763 | 11/1989 | Holen et al. | 436/45 |
| 4,902,479 | 2/1990 | Bri Kus | 422/72 |
| 5,061,446 | 10/1991 | Guigan | 422/64 |
| 5,110,552 | 5/1992 | Guligan | 422/64 |
| 5,112,284 | 5/1992 | Braynin et al. | 210/782 |
| 5,229,297 | 7/1993 | Schnipelsky et al. | 436/94 |
| 5,256,376 | 10/1993 | Callan et al. | 422/102 |
| 5,422,271 | 6/1995 | Chen et al. | 435/287 |

FOREIGN PATENT DOCUMENTS 0402994  12/1990  European Pat. Off. .

*Primary Examiner*—Bradley L. Sisson
*Attorney, Agent, or Firm*—David W. Highet, Esq.

[57] ABSTRACT

A disposable, self-contained test unit is provided for use in carrying out an immunoassay or an integrated nucleic acid amplification and nucleic acid assay. The test unit includes sample, reagent and waste chambers, and the flow of sample and reagent liquids is controlled by centrifugal force. Different liquids may be caused to flow at different times by locating the chambers at different radial distances from the axis of rotation, and progressively increasing the speed of rotation during the assay procedure. An automated test instrument for receiving and rotating a number of such test units is also disclosed.

29 Claims, 24 Drawing Sheets

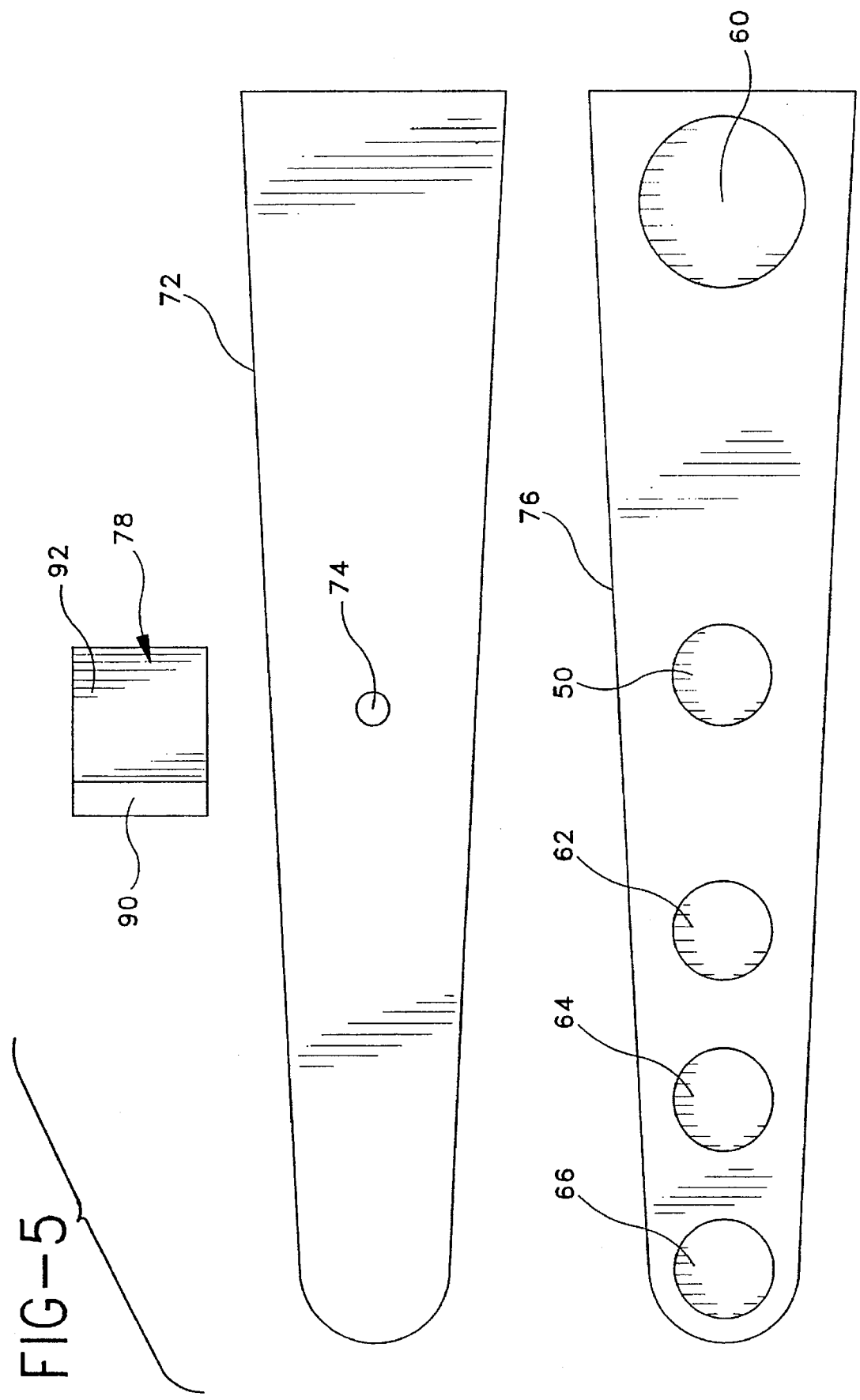

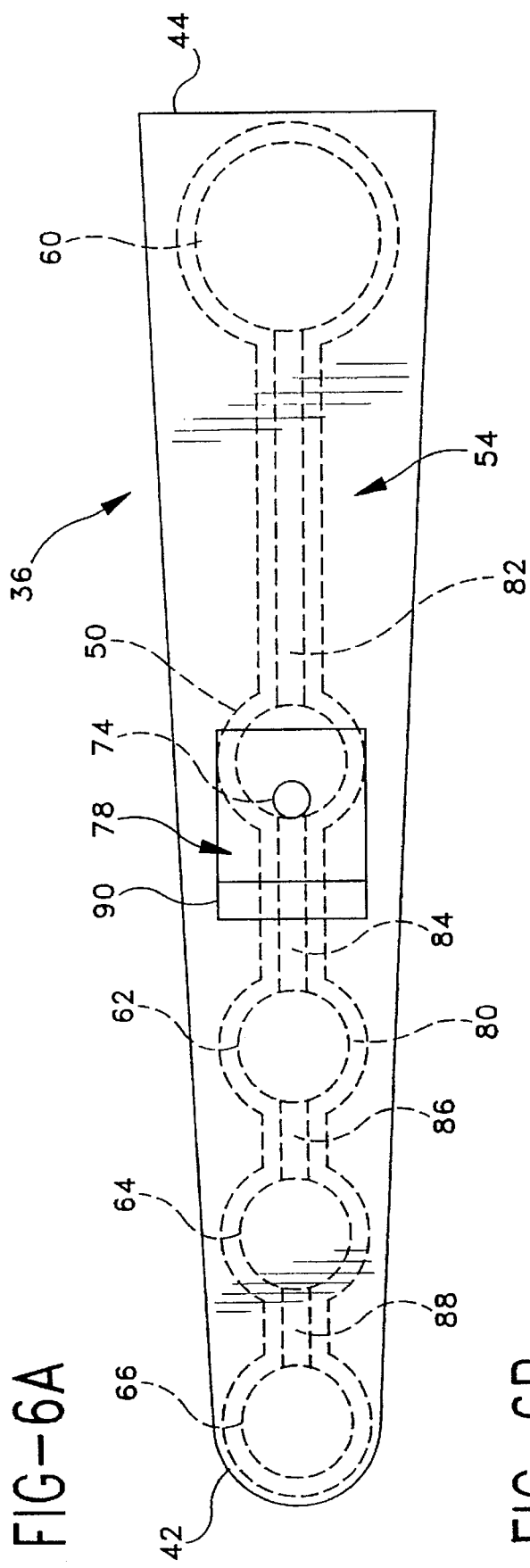
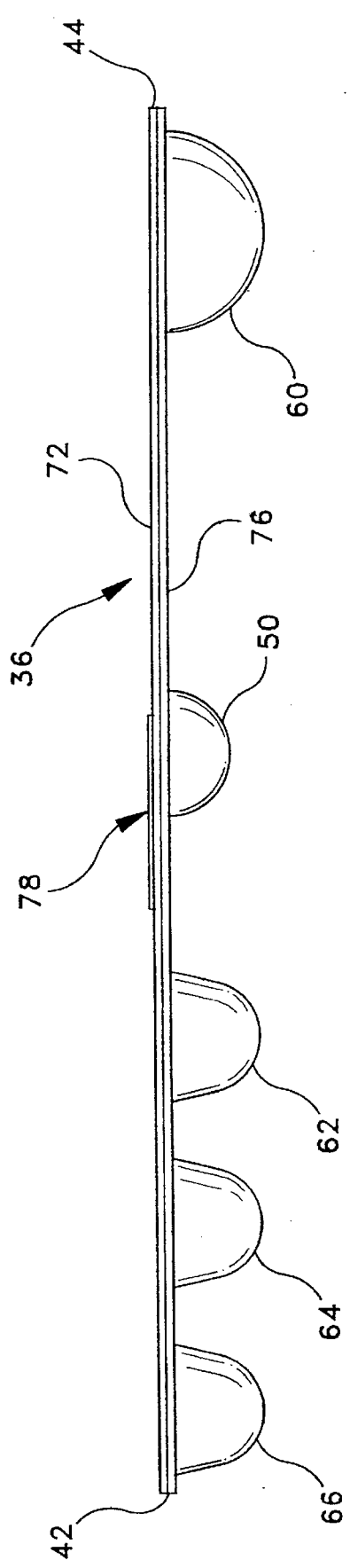
FIG-6A
FIG-6B

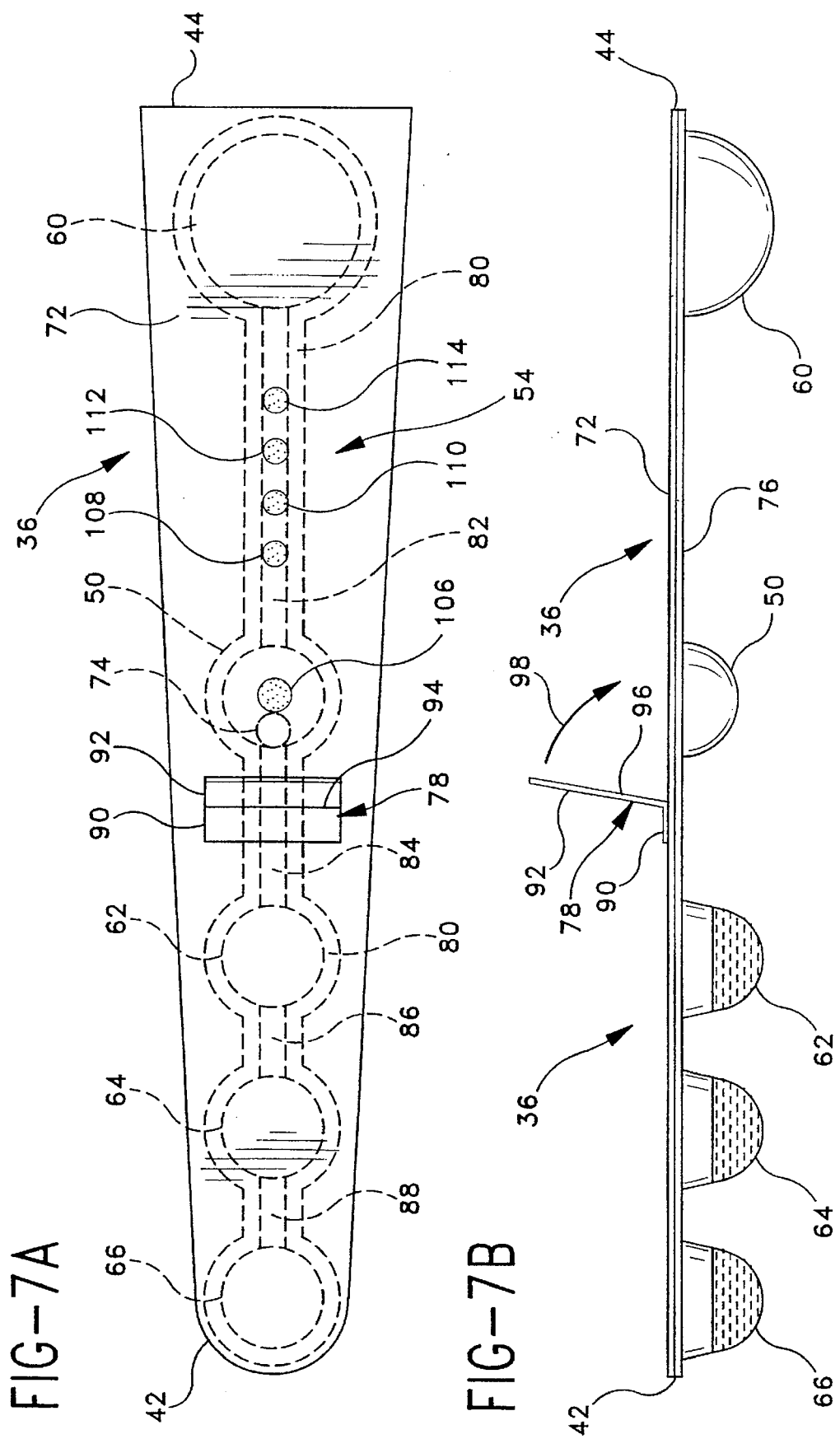

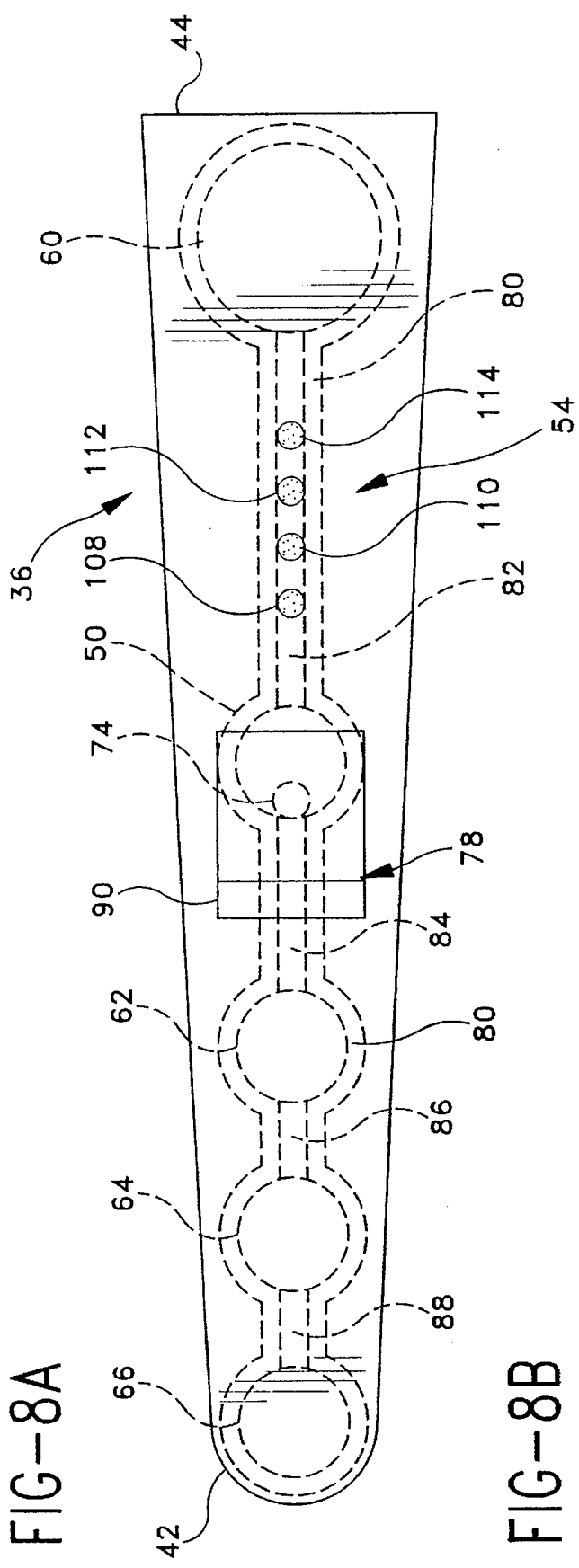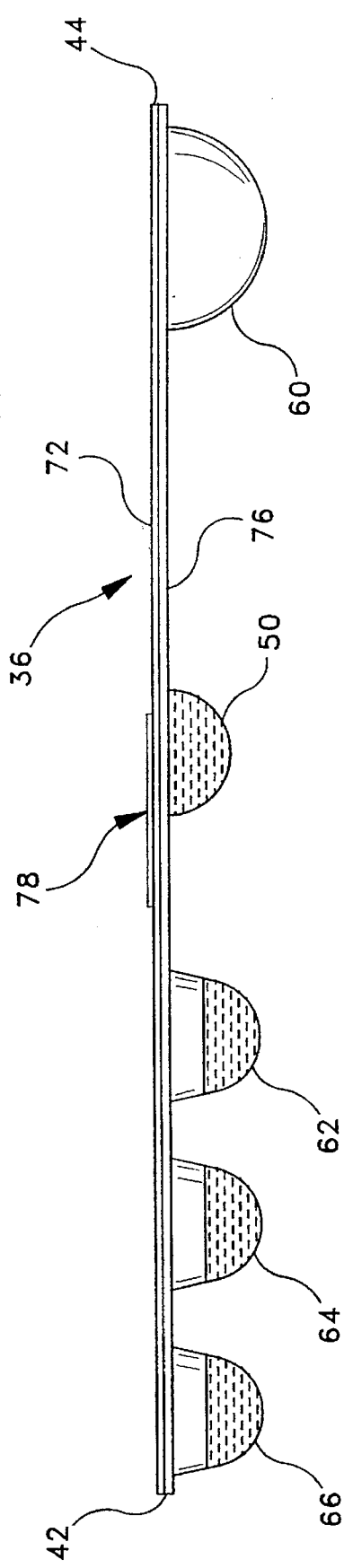

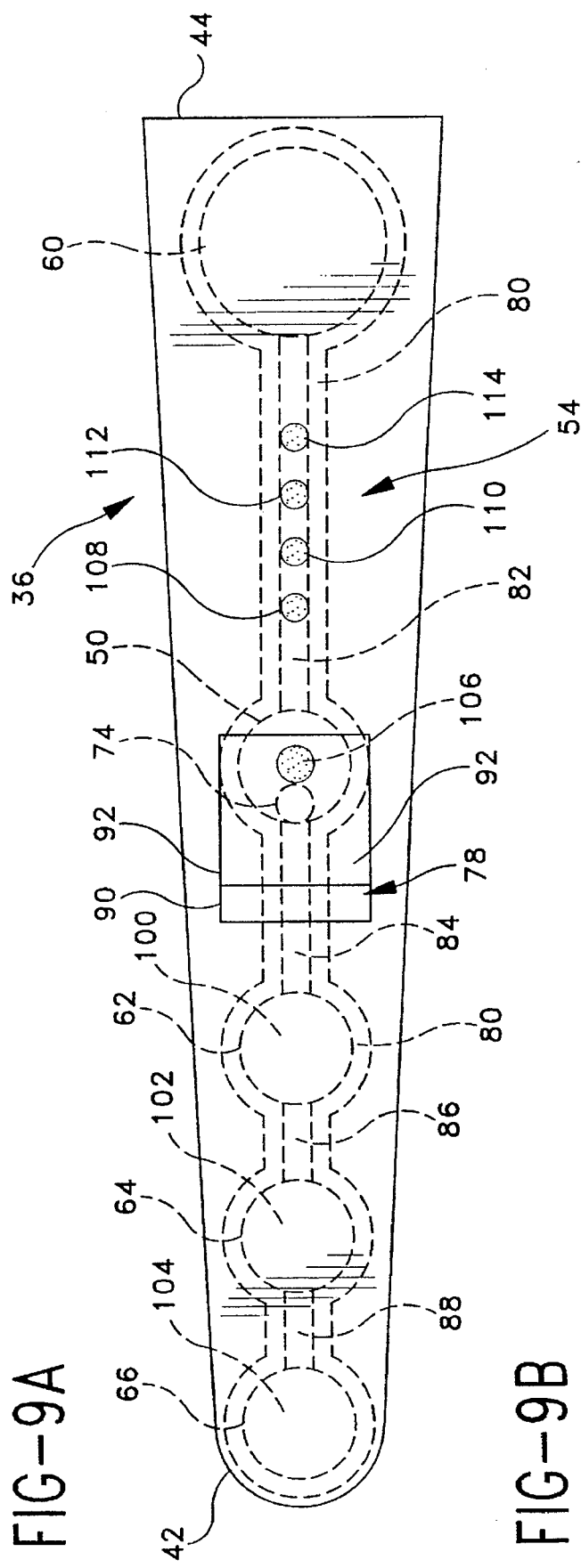
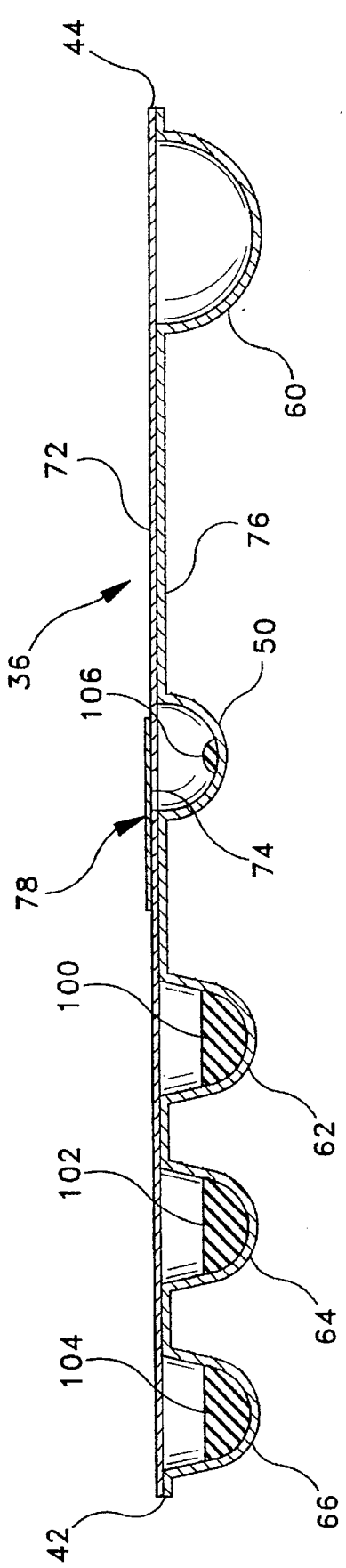

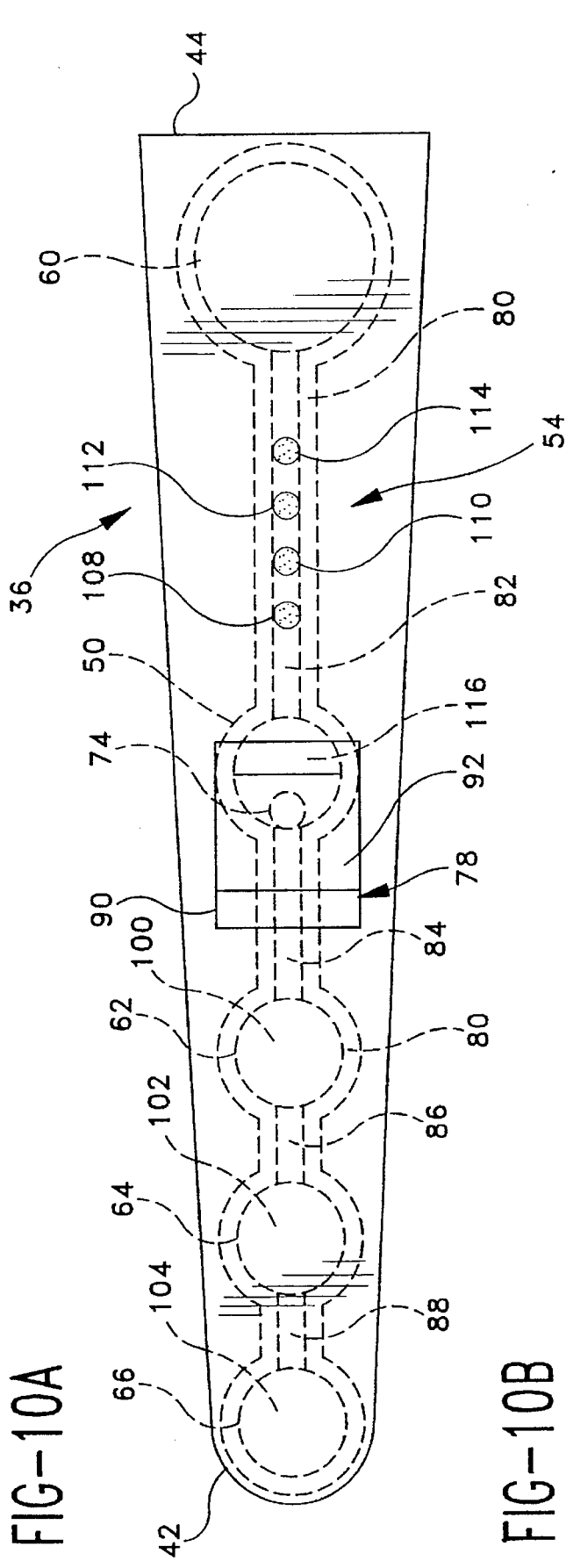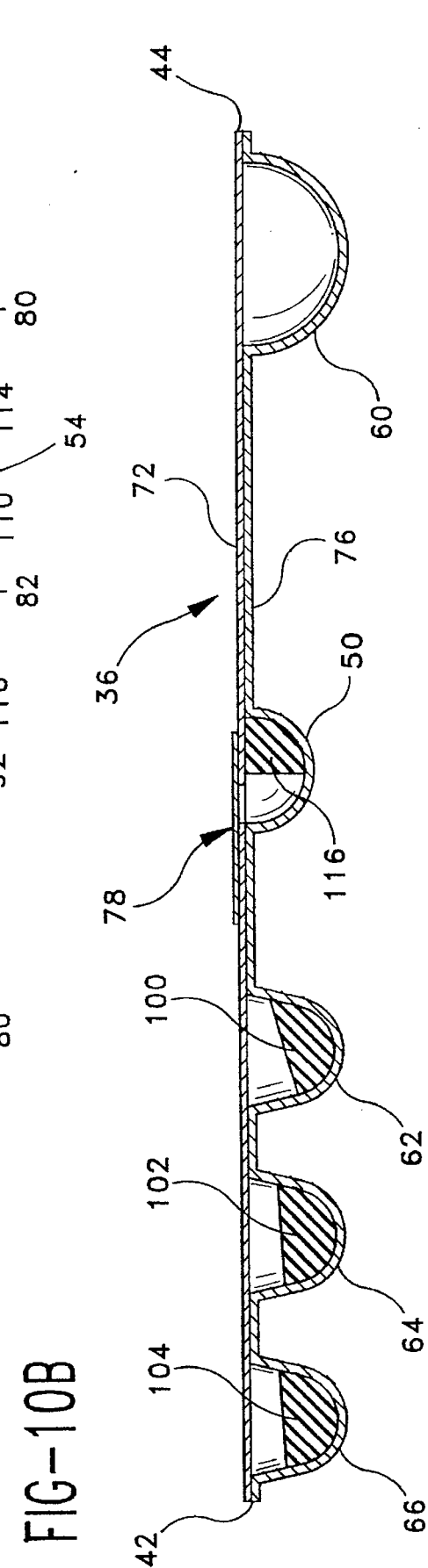

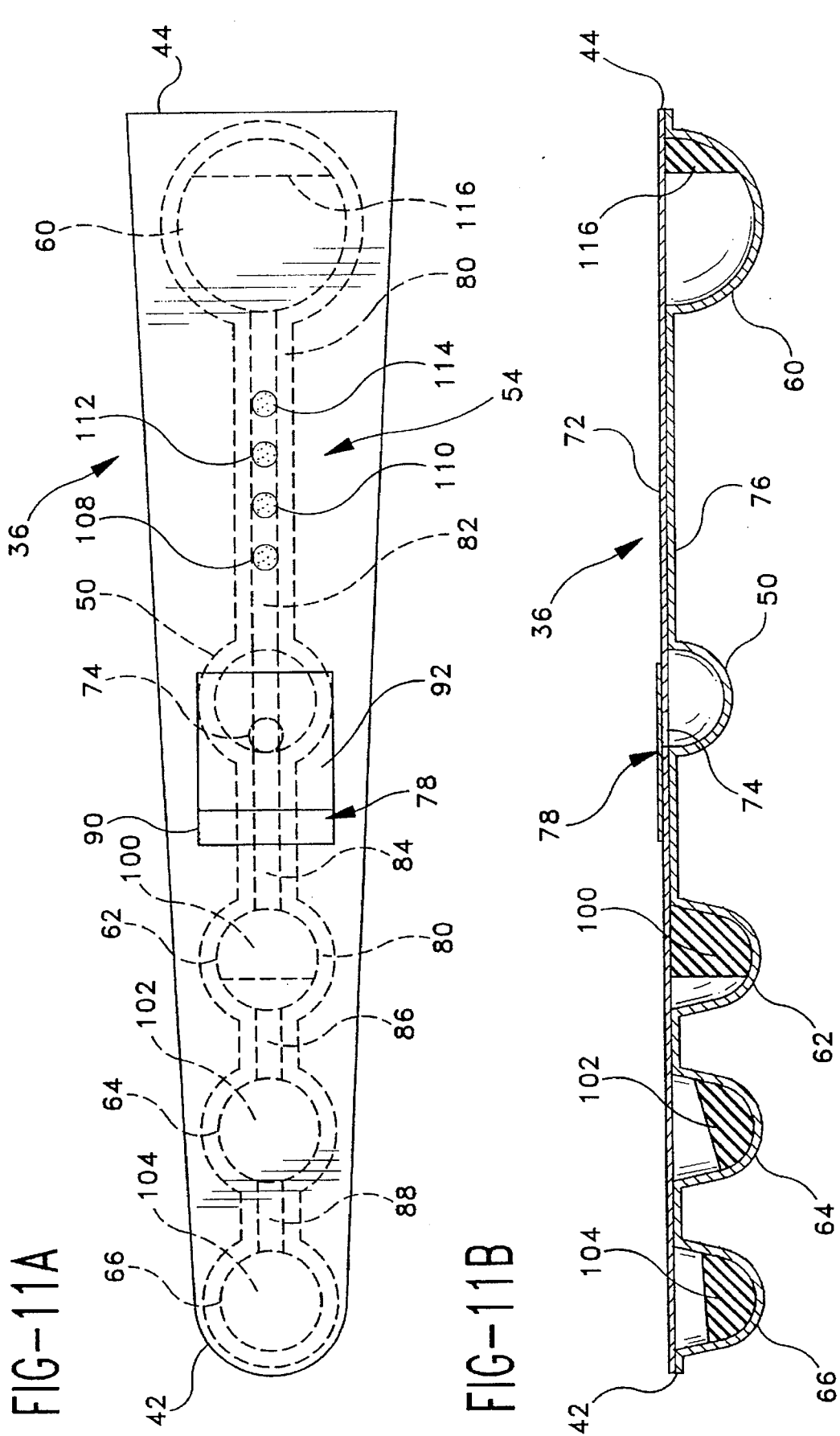

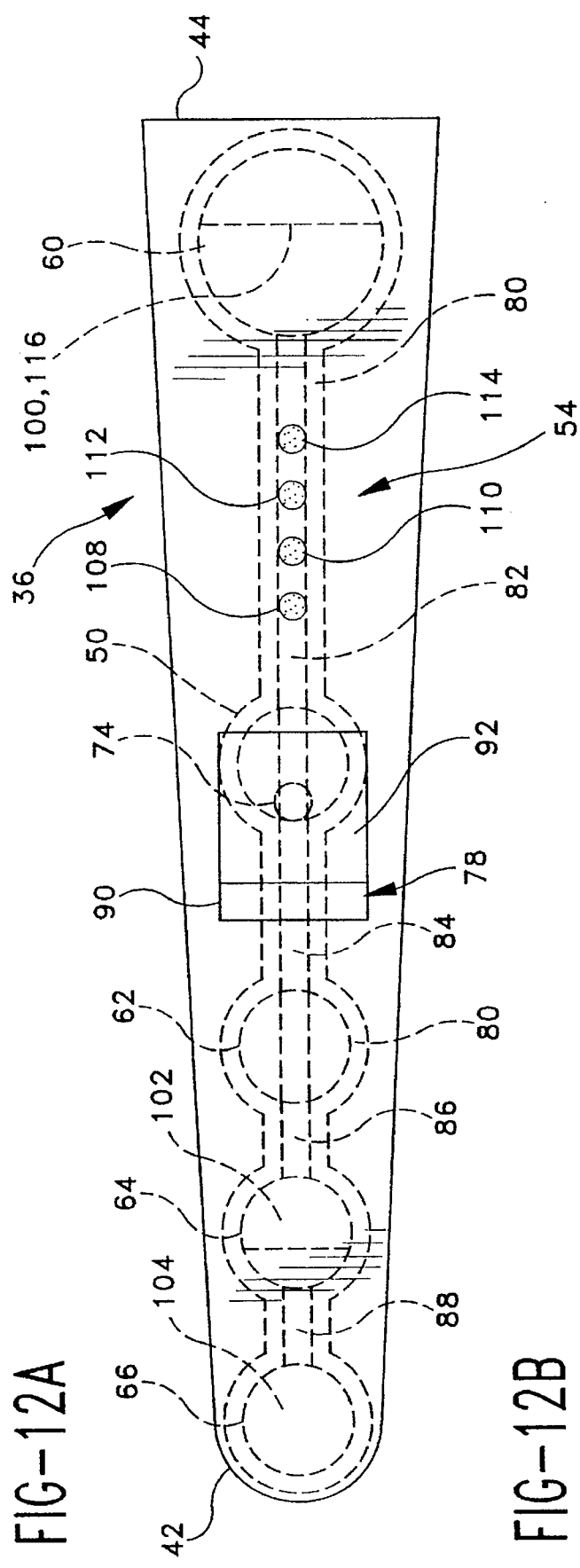
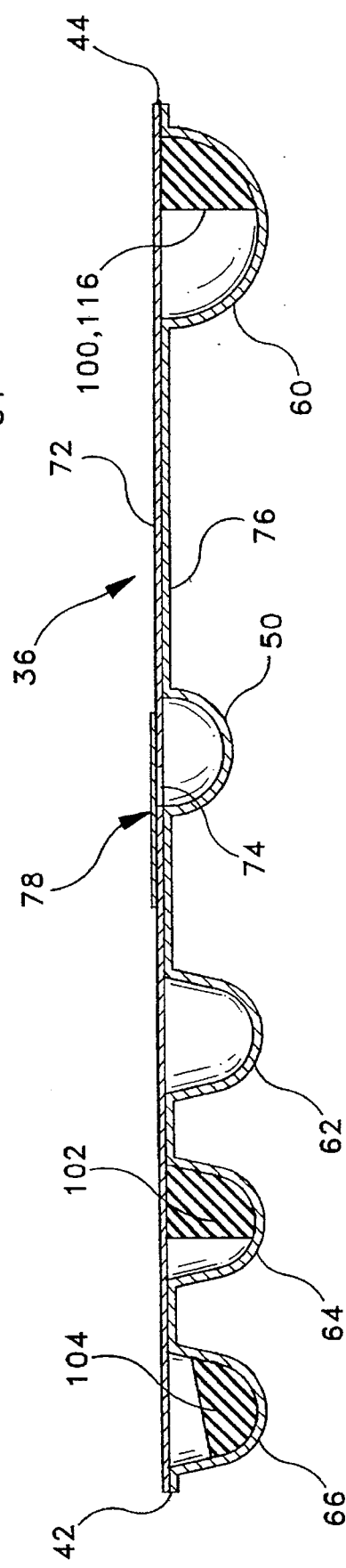

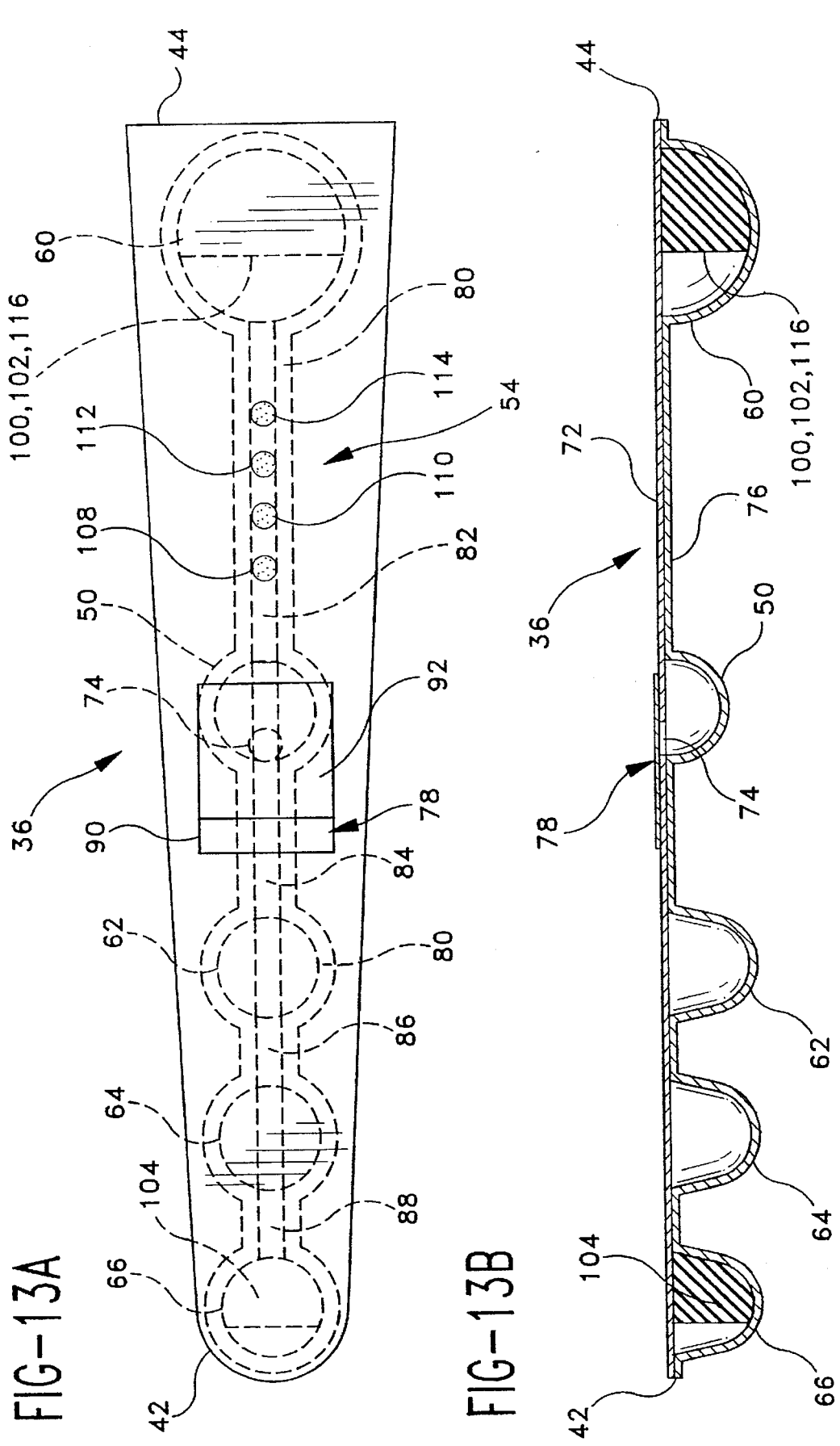

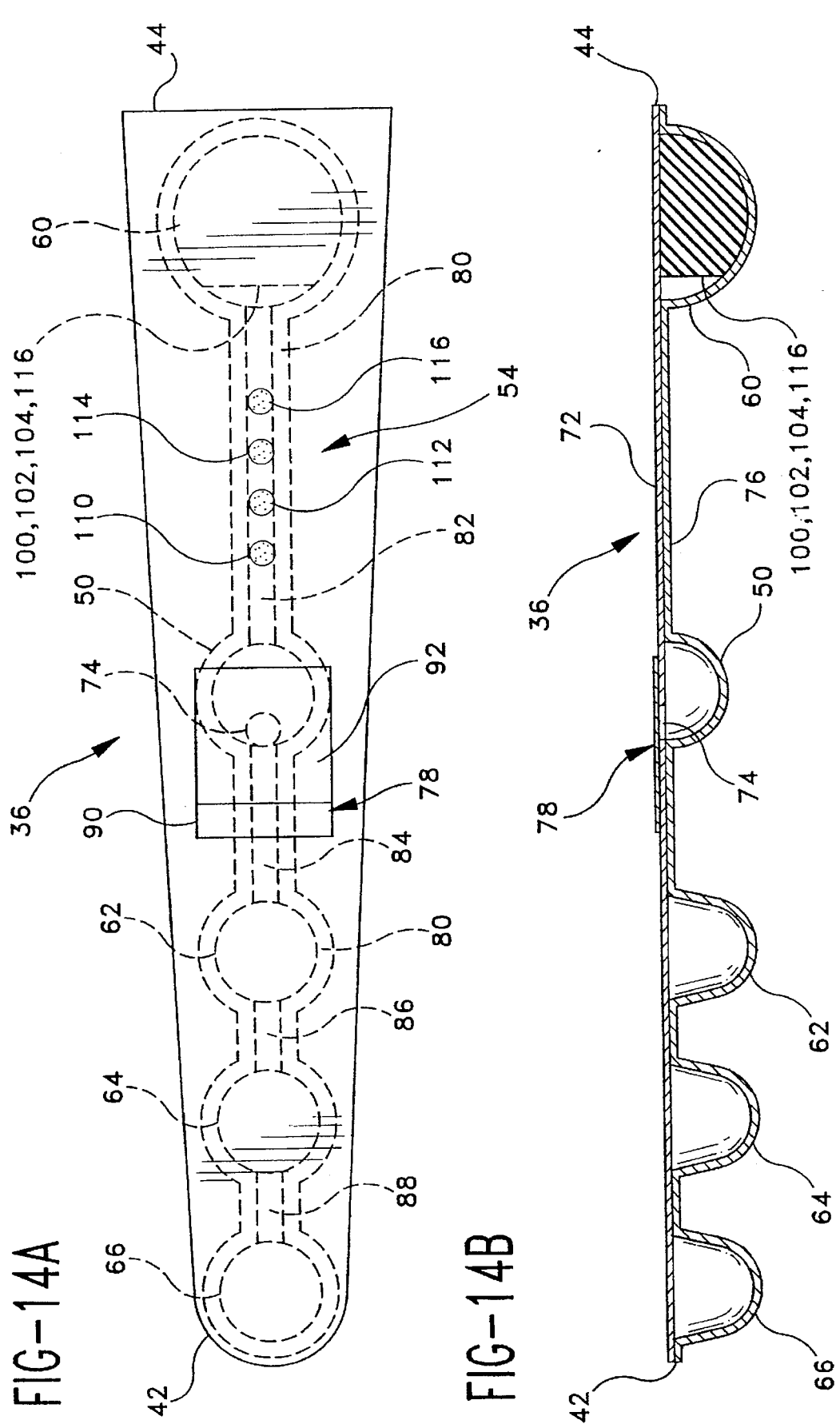

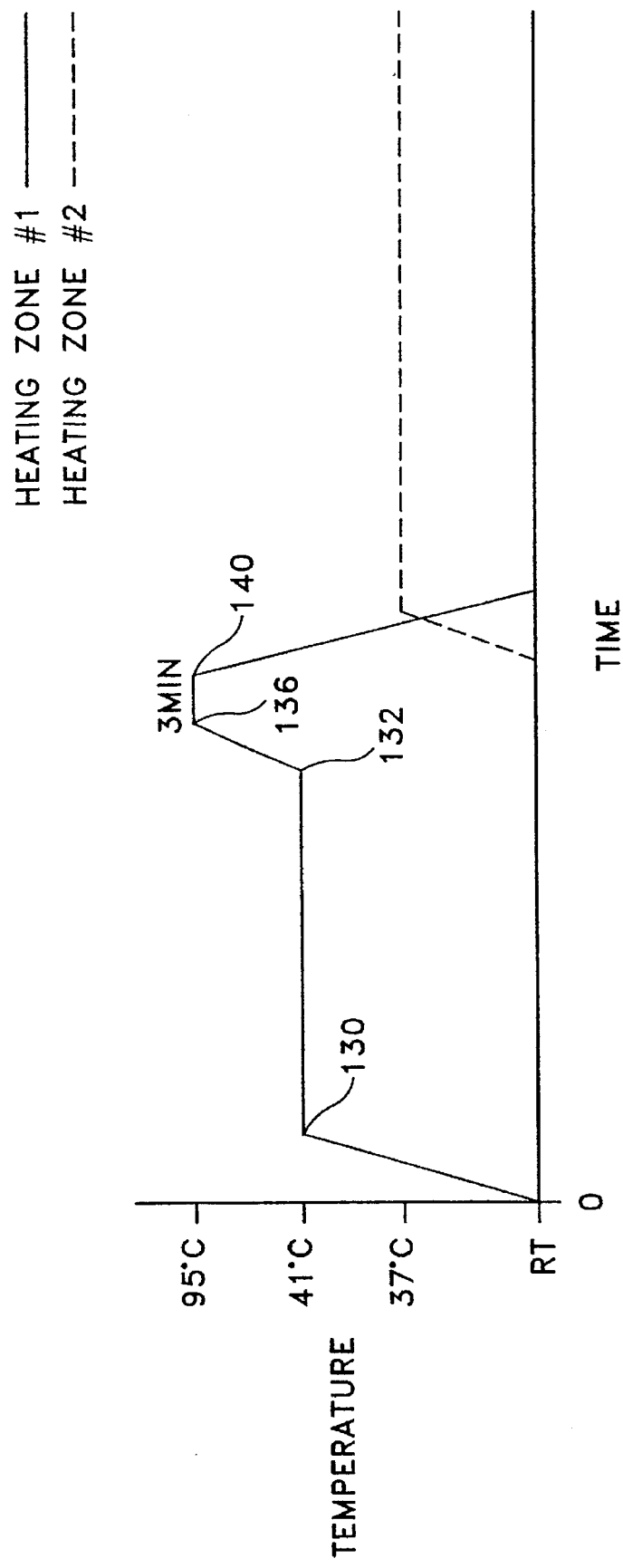

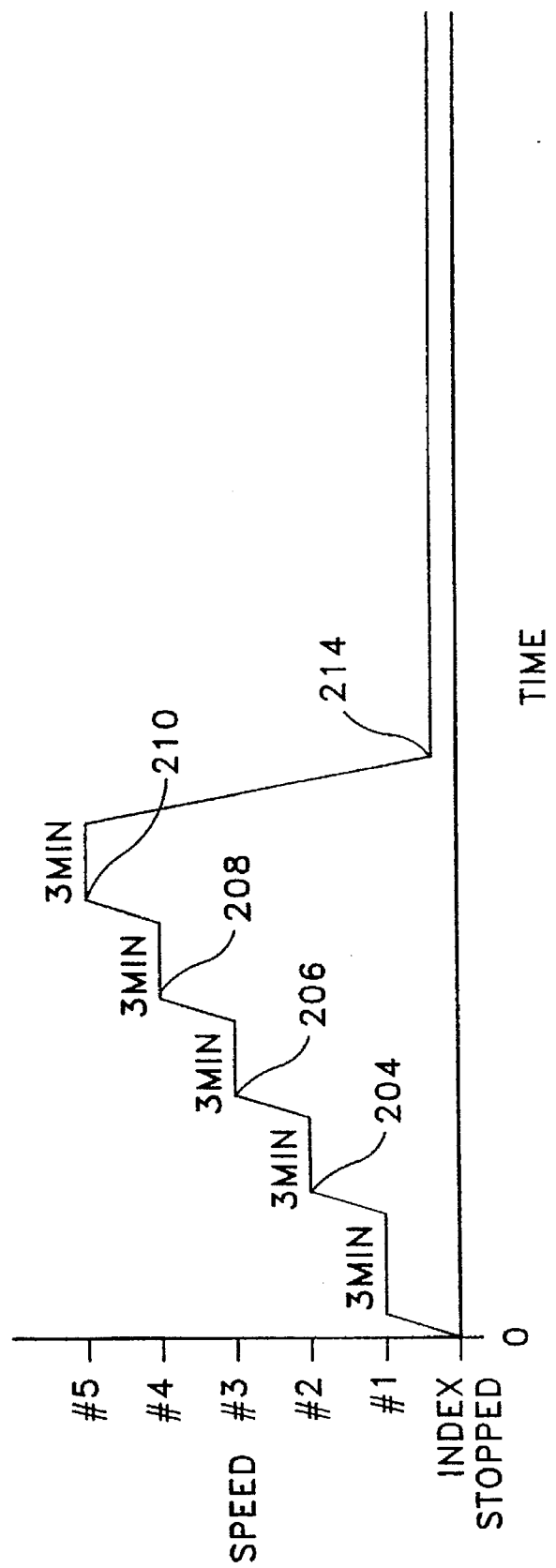

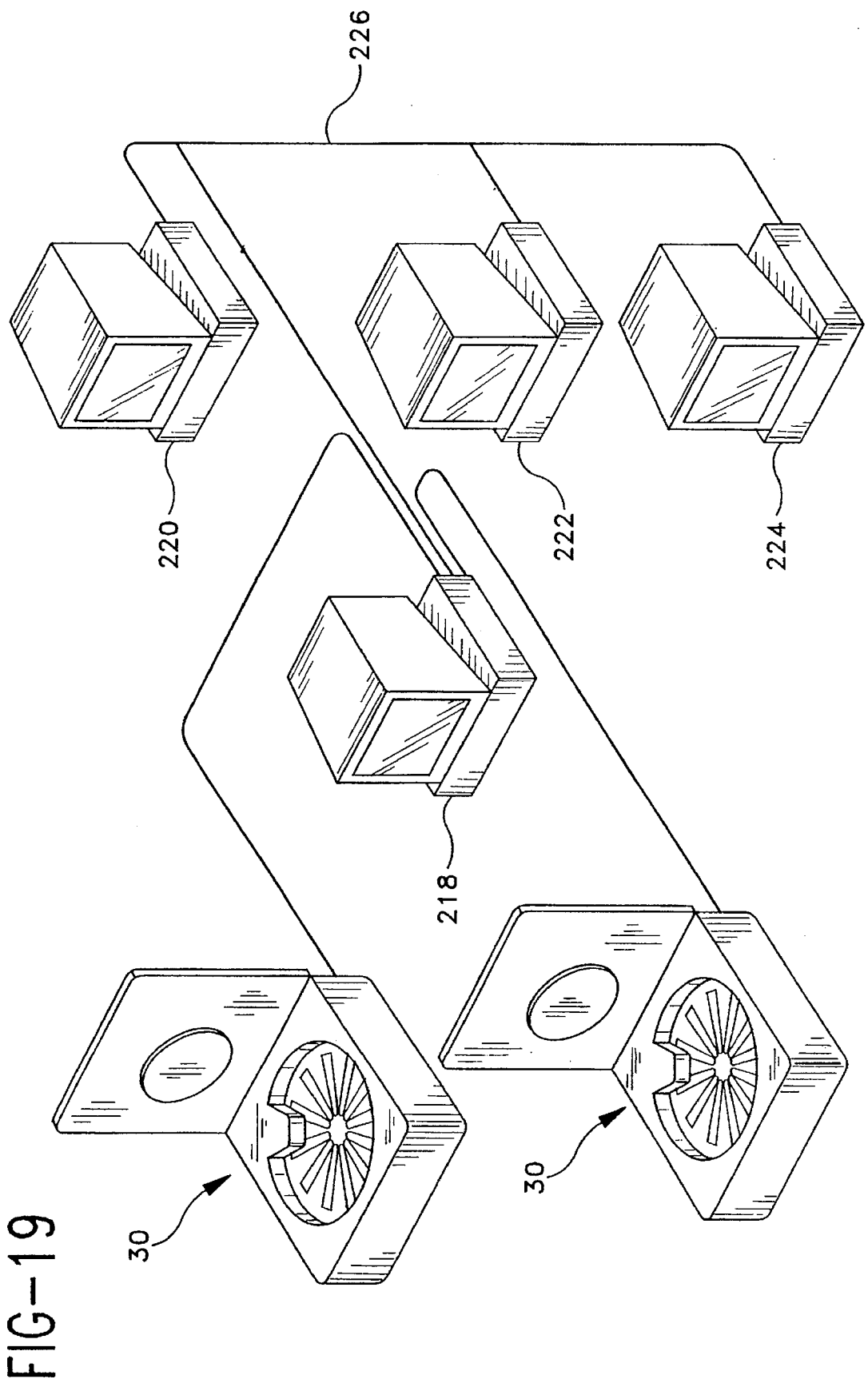

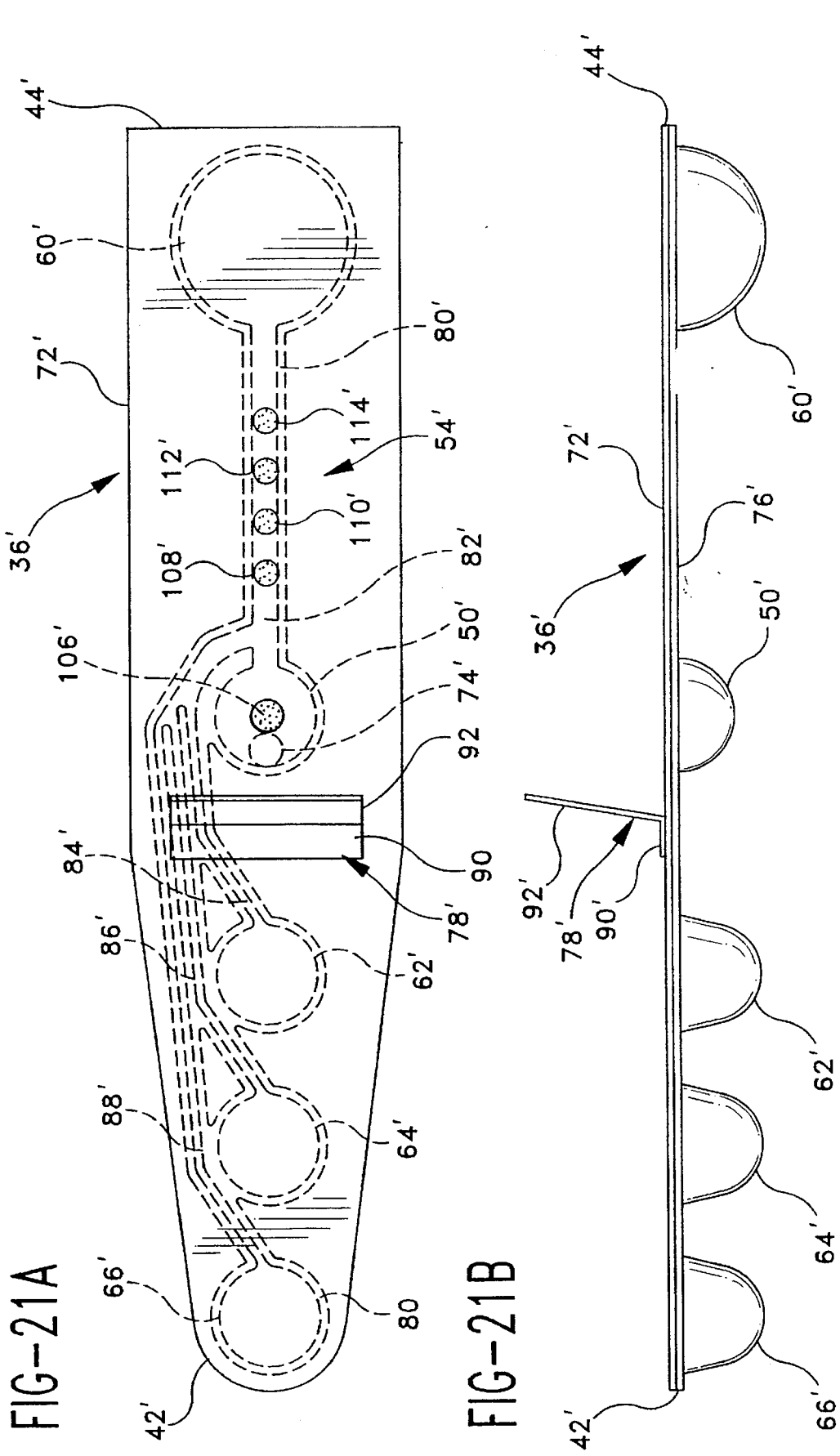

METHOD AND APPARATUS FOR FULLY AUTOMATED NUCLEIC ACID AMPLIFICATION, NUCLEIC ACID ASSAY AND IMMUNOASSAY

CROSS-REFERENCE TO RELATED APPLICATION

Related subject matter is disclosed and claimed in a co-pending U.S. patent application of Hugh V. Cottingham, Ser. No. 08/213,304, filed on Mar. 14, 1994 and entitled "Nucleic Acid Amplification Method and Apparatus", the disclosure of which is expressly incorporated herein by reference.

FIELD OF THE INVENTION

The present invention relates to methods and apparatus for performing automated clinical diagnostic assays, particularly immunoassays or integrated nucleic acid amplifications and nucleic acid assays, and to a serf-contained, disposable test unit for use in such methods and apparatus.

BACKGROUND OF THE INVENTION

The advent of nucleic acid amplification techniques offers great potential to improve the sensitivity of detection in many areas. One such area is in the detection and identification of human pathogens. The ability to detect as little as one organism makes detection possible at a much earlier stage in the progression of a disease. Unfortunately, while nucleic acid amplification techniques are extremely powerful, they are not simple to perform. Complications with respect to operating parameters, such as precise time-temperature requirements, and possible contamination by amplified nucleic acids have so far restricted these techniques to the research laboratory. In order to make these amplification techniques practical for use in hospitals and clinical laboratories, problems arising from complicated operating parameters and contamination must be resolved. Moreover, for reasons of manufacturing efficiency, and due to the emphasis on reduction of health care costs, it is also desirable to provide a universal platform for nucleic acid amplification, nucleic acid assay, immunoassay and assays using nucleic acid ligands to bind proteins or small molecular weight molecules (hereinafter referred to as nucleic acid ligand based assays). Such nucleic acid ligand based assays may also utilize bi-directional nucleic acid ligand compounds.

One way to meet these objectives is to construct a fully automated system to run the entire nucleic acid amplification and nucleic acid assay (or immunoassay), convert the raw data into clinical results, and report the results through the local area network (LAN) of a laboratory or hospital. In order to make such a system practical, all of the steps involved in the test procedure should preferably be carried out while the liquid biological sample remains confined within a single, disposable test unit. This not only reduces the risk of contamination of the laboratory or hospital environment, but also allows the test procedure to be carried out quickly, inexpensively and without the need for highly skilled personnel.

Unfortunately, existing designs for self-contained test units are not entirely satisfactory, particularly when cost factors are considered. For example, U.S. Pat. No. 5,229,297, to Schnipelsky et al, describes a cuvette for DNA amplification and detection which comprises a plurality of flexible compartments for containing a sample, amplifying reagents and detection reagents, together with passageways connecting the sample and reagent compartments with a detection site and a waste compartment. A roller is used to squeeze or compress the sample and reagent compartments in a desired sequence, thereby forcing the sample and detection reagents through the passageways to the detection site and waste compartment. Temporary seals are used to isolate the sample and reagent compartments from the passageways until sufficient pressure is generated by the roller. Although the disclosed arrangement is advantageous in that the sample remains within the cuvette during amplification and detection, the need for a roller to break the temporary seals and cause the various fluids to flow between compartments makes it difficult to automate the procedure, particularly when a number of samples and cuvettes are to be processed at the same time. In an alternative embodiment of the Schnipelsky et al patent, the fluids are moved between compartments by movable pistons which form a part of the cuvette itself. Again, however, automated processing of several cuvettes at once is difficult with this embodiment, and the need for several pistons in each cuvette renders the cost of the cuvette higher than might be desired.

It is therefore an object of the present invention to provide a fully automated system to perform an integrated nucleic acid amplification and nucleic acid assay, or to perform an immunoassay or nucleic acid ligand based assay.

It is another object of the invention to contain all reagents and components necessary to perform immunoassays or nucleic acid ligand based assays, or integrated nucleic acid amplifications and nucleic acid assays, for a particular sample in a single, disposable test unit.

It is a further object of the invention to provide a disposable test unit which can be automatically closed and permanently sealed to prevent contamination of the laboratory environment from amplified nucleic acids.

It is a still further object of the invention to support nucleic acid amplification multiplexing and report a multiplicity of nucleic acid assay results using a single, disposable test unit and a single clinical sample.

It is yet another object of the invention to support multiplexed immunoassays and report a multiplicity of immunoassay results using a single, disposable test unit and a single clinical sample.

It is yet another object of the invention to support multiplexed nucleic acid ligand based assays and report a multiplicity of nucleic acid ligand based assay results using a single disposable test unit in a single clinical sample.

It is a further object of the invention to provide an automated clinical assay apparatus which can be directly interfaced with a laboratory or hospital LAN for the purpose of reporting and archiving clinical results with minimum delay and human intervention.

SUMMARY OF THE INVENTION

In accordance with the present invention, the disadvantages and limitations of the prior art are substantially avoided by providing a disposable, self-contained test unit in which the flow of sample and reagent liquids can be controlled by centrifugal force applied by a relatively simple rotating apparatus, thereby avoiding the need for rollers, pistons and other complex mechanisms. This allows the test unit to be made relatively simple and inexpensive in construction, and also allows many samples to be assayed simultaneously by mounting a plurality of test units for rotation in the same apparatus. The invention is also directed to an apparatus which is capable of receiving a number of such test units for rotation, in order to allow a number of liquid biological samples to be assayed simultaneously and automatically.

In one aspect, therefore, the present invention is directed to an improved test unit for carrying out a clinical diagnostic assay. The test unit comprises a sample chamber for receiving a liquid biological sample to be assayed, a closure for sealing the sample chamber, a sealed waste chamber for receiving the liquid biological sample from the sample chamber, and a liquid flow path for the liquid biological sample extending between the sample chamber and the waste chamber. The test unit further comprises non-frangible flow control means for preventing the flow of the liquid biological sample through the liquid flow path in the absence of a force applied to the sample, and for permitting the liquid biological sample to flow through the liquid flow path when at least a predetermined minimum force is applied to the sample. Since the force required to overcome the non-frangible flow control means will ordinarily be less than that required to break a frangible seal, the required force can, for example, comprise centrifugal force that is produced by rotating the test unit about an axis. The test unit further comprises at least one immobilized reagent disposed in the liquid flow path for contacting the liquid biological sample as the sample flows from the sample chamber to the waste chamber. In a preferred embodiment, the immobilized reagent comprises a nucleic acid probe, and a dried amplification reagent is disposed in the sample chamber for carrying out nucleic acid amplification in the liquid biological sample before the sample leaves the sample chamber. In other embodiments, reagents suitable for carrying out an immunoassay or nucleic acid ligand based assays can be provided in the test unit.

In another aspect, the present invention is directed to an improved test unit in which the flow of a liquid biological sample can be controlled by rotating the test unit to produce centrifugal force. The test unit comprises a sample chamber for receiving a liquid biological sample to be assayed, a closure for sealing the sample chamber, a sealed waste chamber spaced from the sample chamber for receiving the liquid biological sample from the sample chamber, and a liquid flow path for the liquid biological sample extending between the sample chamber and the waste chamber. The liquid flow path has a non-reversing configuration, with each successive incremental section of the channel in the direction of flow being further from (or, at a minimum, no closer to) the intended axis of rotation of the test unit. The test unit further comprises at least one immobilized reagent disposed in the liquid flow path for contacting the liquid biological sample as the sample flows from the sample chamber to the waste chamber. By virtue of the spacing between the sample chamber and the waste chamber and the non-reversing configuration of the liquid flow path, a liquid biological sample can be caused to flow from the sample chamber to the waste chamber by rotating the test unit about an axis and thereby applying centrifugal force to the sample in the direction from the sample chamber to the waste chamber.

In a further aspect, the present invention is directed to a method for carrying out a clinical diagnostic assay. The method comprises the steps of providing a test unit having a sample chamber, a waste chamber spaced from the sample chamber, a liquid flow path extending between the sample chamber and the waste chamber, and an immobilized reagent disposed in the liquid flow path; introducing a liquid biological sample into the sample chamber;, mounting the test unit for rotation about an axis with the test unit oriented such that rotation about the axis causes centrifugal force to be applied to the liquid biological sample in a direction from the sample chamber to the waste chamber;, rotating the test unit about the axis to cause the liquid biological sample to flow through the liquid flow path from the sample chamber to the waste chamber by centrifugal force, and to thereby contact the immobilized reagent; and detecting the presence or absence of a chemical or biological component in the liquid biological sample based on a response or lack of response of the immobilized reagent to the liquid biological sample. In a preferred embodiment of the inventive method, the test unit is also provided with at least one reagent chamber containing a liquid reagent, and the liquid reagent is caused to flow from the reagent chamber to the liquid flow path by increasing the speed of rotation of the test unit after the liquid biological sample has passed through the liquid flow path.

In a still further aspect of the present invention, an apparatus is provided for performing a plurality of clinical diagnostic assays substantially simultaneously. The apparatus comprises a rotatable holder for carrying a plurality of test units for rotation about an axis, a source of rotary power for rotating the rotatable holder about the axis, and a plurality of removable test units carried by the rotatable holder and spaced circumferentially about its axis of rotation. Each of the test units comprises a sample chamber for receiving a liquid biological sample to be assayed, a waste chamber for receiving the liquid biological sample from the sample chamber, a liquid flow path extending between the sample chamber and the waste chamber, an immobilized reagent disposed in the liquid flow path, and, optionally, one or more reagent chambers for containing liquid detection reagents. Each of the test units is oriented with respect to the rotatable holder in a manner such that the sample chamber is located closer to the axis of rotation than the waste chamber, in order to cause the liquid biological sample to flow through the liquid flow path from the sample chamber to the waste chamber, and to thereby be brought into contact with the immobilized reagent, when centrifugal force is exerted on the liquid biological sample by rotation of the holder. The apparatus also comprises at least one sensor for detecting responses by the immobilized reagents in the test units to the presence of a chemical or biological component in the liquid biological samples. Preferably, the source of rotary power can be selectively operated at two or more different rotational speeds, so that liquids can be caused to flow in sequence from the sample and reagent chambers by increasing the speed of rotation of the rotatable holder in predetermined increments sufficient to overcome the flow resistance of liquid flow paths extending from the respective chambers.

BRIEF DESCRIPTION OF THE DRAWINGS

The various objects, advantages and novel features of the invention will be more readily appreciated from the following detailed description when read in conjunction with the appended drawing figures, in which:

FIG. 5 is an exploded view of the disposable test unit shown in FIG. 4, illustrating the manner in which it is constructed;

FIGS. 6A and 6B are plan and side views, respectively, of the disposable test unit shown in FIG. 4;

FIGS. 7A and 7B are enlarged plan and side views, respectively, of the disposable test unit of FIG. 4, with the adhesive seal or closure device shown in the open position;

FIGS. 8A and 8B are enlarged plan and side views, respectively, of the disposable test unit of FIG. 4, with the adhesive seal or closure device shown in the closed position;

FIGS. 9A and 9B are enlarged plan and side sectional views, respectively, of the disposable test unit of FIG. 4 as it might appear prior to the start of a clinical diagnostic assay, with the liquid biological sample not yet having been introduced into the sample chamber;

FIGS. 10A, 10B and 10C are enlarged plan, side sectional and fragmentary views, respectively, of the disposable test unit of FIG. 4 as it might appear immediately after the start of a clinical diagnostic assay, with the liquid biological sample beginning to flow from the sample chamber to the waste chamber;

FIGS. 11A and 11B are enlarged plan and side sectional views, respectively, of the disposable test unit of FIG. 4 as it might appear during a later stage of a clinical diagnostic assay, with a first liquid reagent beginning to flow from a first reagent chamber to the waste chamber;

FIGS. 12A and 12B are enlarged plan and side sectional views, respectively, of the disposable test unit of FIG. 4 as it might appear during a still later stage of a clinical diagnostic assay, with a second liquid reagent beginning to flow from a second reagent chamber to the waste chamber;

FIGS. 13A and 13B are enlarged plan and side sectional views, respectively, of the disposable test unit of FIG. 4 as it might appear during the final stage of a clinical diagnostic assay, with a third liquid reagent beginning to flow from a third reagent chamber to the waste chamber;

FIGS. 14A and 14B are enlarged plan and side sectional views, respectively, of the disposable test unit of FIG. 4 as it might appear after the completion of a clinical diagnostic assay, with the liquid biological sample and all reagents having flowed into the waste chamber;

FIGS. 18A and 18B are graphs illustrating the manner in which the rotational speed and temperature of the disposable test units are varied over time during an immunoassay or nucleic acid ligand based assay, using the automated test instrument of FIG. 1;

FIG. 19 is a schematic diagram illustrating the manner in which two or more automated test instrument of the type illustrated in FIG. 1 may be controlled by a single host computer, which can in turn be connected to the local area network (LAN) of a hospital or clinical laboratory;

FIGS. 21A and 21B are enlarged plan and side views similar to FIGS. 7A and 7B, respectively, illustrating a modified embodiment of the disposable test unit.

Throughout the drawings, like reference numerals will be understood to refer to like parts and components.

DETAILED DESCRIPTION OF THE PREFERRED EMBODIMENTS

Figure 1:
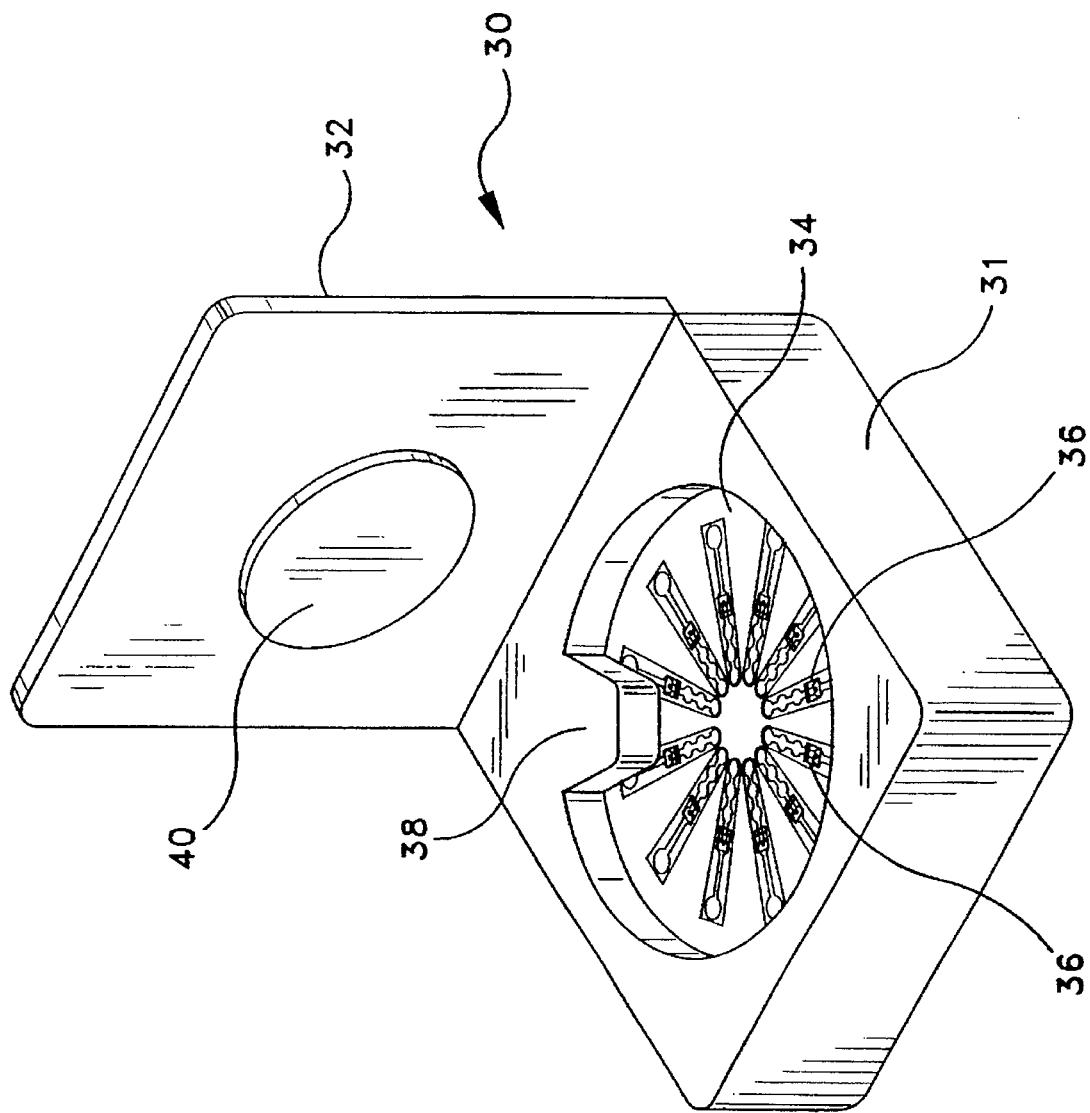
FIG. 1 is a perspective view of an automated test instrument which may be used to carry out a number of simultaneous clinical diagnostic assays in accordance with the present invention, with the lid or cover of the instrument shown in the open position to illustrate the placement of the disposable test units inside.

An automated test instrument 30 for carrying out a plurality of clinical diagnostic assays in accordance with the present invention is illustrated in FIG. 1. The apparatus 30 is, in a preferred embodiment, approximately 12 inches wide by 12 inches deep and 4.5 inches high. It includes a bottom portion 31 and a hinged lid 32. A circular rotor 34 housed in the bottom portion 31 receives and rotates a number of removable, radially positioned, disposable (single-use) test units 36. The rotor 34 revolves in a plane parallel to the top of the apparatus 30 and causes centrifugal force to be exerted upon the disposable test units 36. Positioned above the rotor 34 is an optical detector housing 38, which contains light sources and optical detectors for detecting optical responses by immobilized reagents contained in the disposable test units 36. The disposable test units 36 are automatically sealed and retained in place on the rotor 34 by means of a freely rotating clamp 40 carried by the lid 32.

Figure 2:
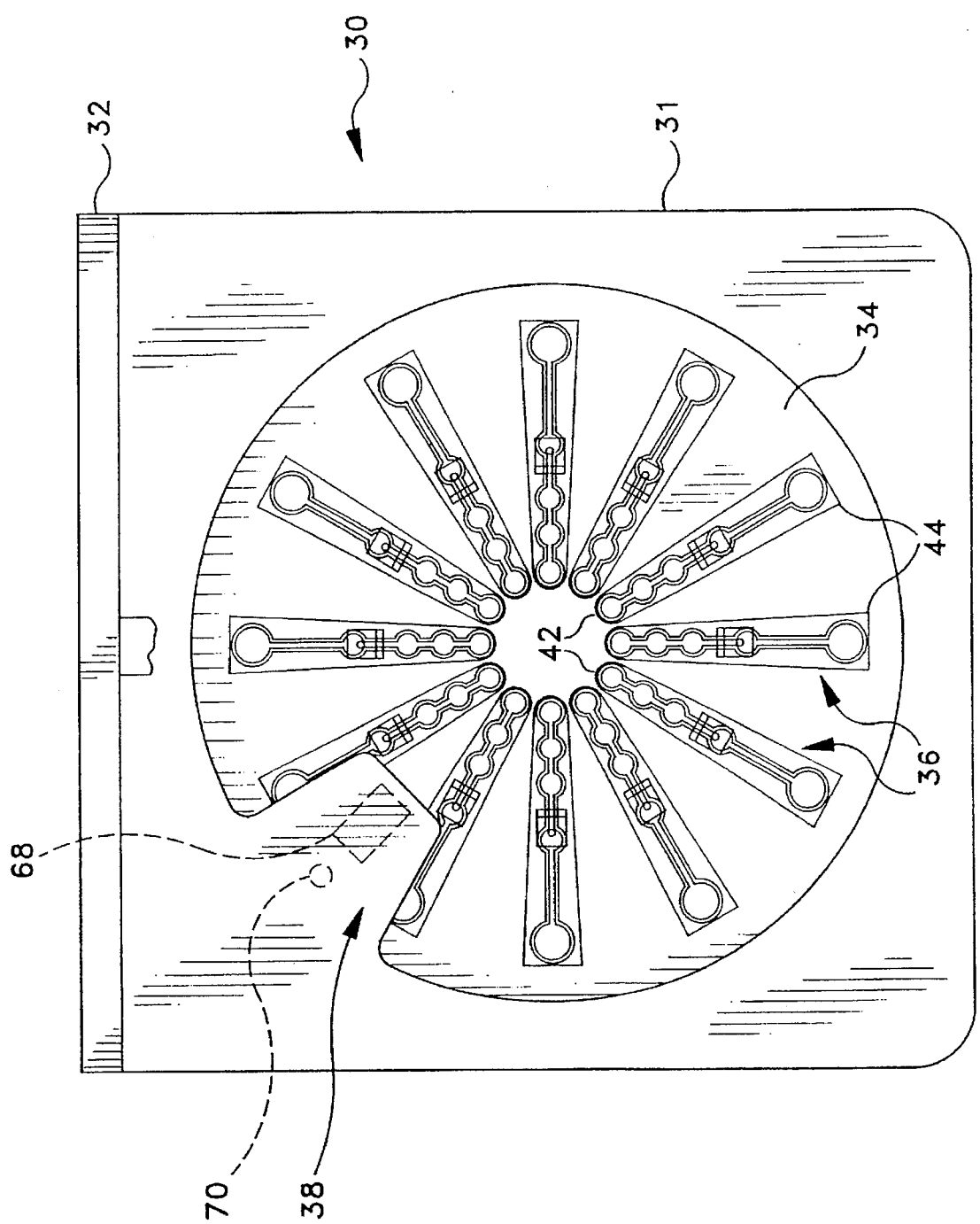
FIG. 2 is an enlarged plan view of the automated test instrument of FIG. 1, showing the location of the optical detectors which are used to detect responses by the immobilized reagents located in the disposable test units.

FIG. 2 more clearly shows the radial positioning of the disposable test units 36 on the rotor 34. The rotor 34 preferably has a diameter of about 10 inches and the disposable test units 36 are each preferably about 3.7 inches long by about 0.45 inches wide at the rounded (inner) end 42 and about 0.8 inches wide at the square (outer) end 44. The rotor 34 accommodates 12 disposable test units 36, arranged in a circumferential array of one disposable test unit every 30 degrees. The optical detector housing 38 is positioned at a fixed location so that each disposable test unit 36 can be scanned in turn as it passes by.

Figure 3:
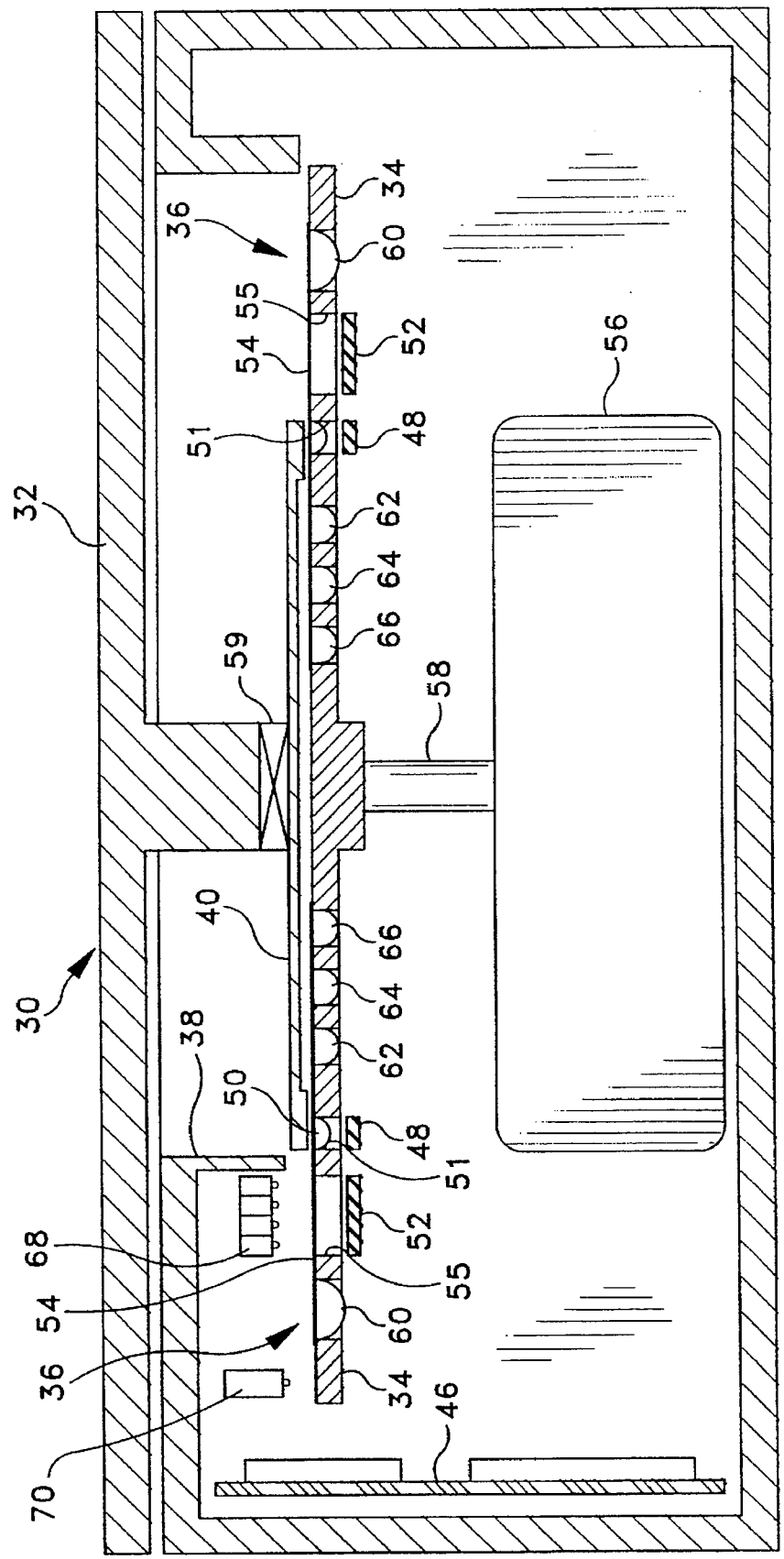
FIG. 3 is an enlarged cross-sectional view of the automated test instrument of FIG. 1, illustrating the locations of the drive motor and other internal components of the instrument.

FIG. 3 is a cross-sectional view of the apparatus 30. A microcontroller board 46 provides suitable control of the electrical components of the apparatus 30. A fixed, first ring-shaped infrared heater 48 is located proximate to the underside of the rotor 34 at a point where the sample/ amplification chambers 50 of the disposable test units 36 are exposed through holes 51 in the rotor 34. Infrared heating of the chambers 50 is controlled by the microcontroller board 46. A second fixed, ring-shaped infrared heater 52 is located proximate to the underside of the rotor 34 at a point where immobilized reagents disposed at detection sites 54 of the disposable test units 36 are exposed through holes 55 in the rotor 34. Infrared heating of the detection sites 54 is also controlled by the microcontroller board 46. It will be appreciated from FIG. 3 that the holes 51 and 55 are part of a radial pattern of holes which are formed in the rotor 34 for receiving various portions of each disposable test unit 36, including the sample chamber 50 and additional chambers 60, 62, 64 and 66 to be described shortly. These holes allow the sample chamber 50 and detection site 54 to be exposed to the respective infrared heaters 48 and 52 as already described, and also assist in locating the disposable test units 36 at the proper angular positions on the rotor 34. If desired, the infrared heaters 48 and 52 can be incorporated into the rotor 34, and in that event the holes 51 and 55 may be replaced by cavities formed in the top surface of the rotor 34.

With continued reference to FIG. 3, a motor 56 and shaft 58 rotate the rotor 34 at various selected speeds to apply predetermined centrifugal forces to the disposable test units 36. The rotating clamp 40 is attached to the lid 32 by means of a rotatable bearing assembly 59, and maintains the disposable test units 36 on the rotor 34 during its rotation. The rotating clamp 40 also effects automatic sealing of the sample ports of the disposable test units 36, as will be described in more detail hereinafter. Positioned above the rotor 34 in the optical detector housing 38 is a first optical assembly 68 which provides illumination and detection of the reacted immobilized chemical reagents contained in the disposable test units 36. The optical assembly 68 has a number of sections as shown, with each section located above one of the immobilized reagent spots (not shown) at the detection site 54 of the test unit 36 positioned below the assembly 68. Depending upon the type of detection technology employed, the optical assembly 68 will typically contain (either in each section or as a common component for all sections) a xenon or laser diode light source; a photomultiplier tube, CCD line array or photodiode; and interference filters, lenses, shutters and other optical elements necessary for the acquisition of the optical output of the immobilized chemical reagents in the disposable test units 36. A second optical assembly 70 is also positioned above the rotor and is for the purpose of detecting marks or notches (not shown) at the edge of the rotor 34, to indicate when a particular disposable test unit 36 is properly indexed to be detected by the first optical assembly 68.

Figure 4:
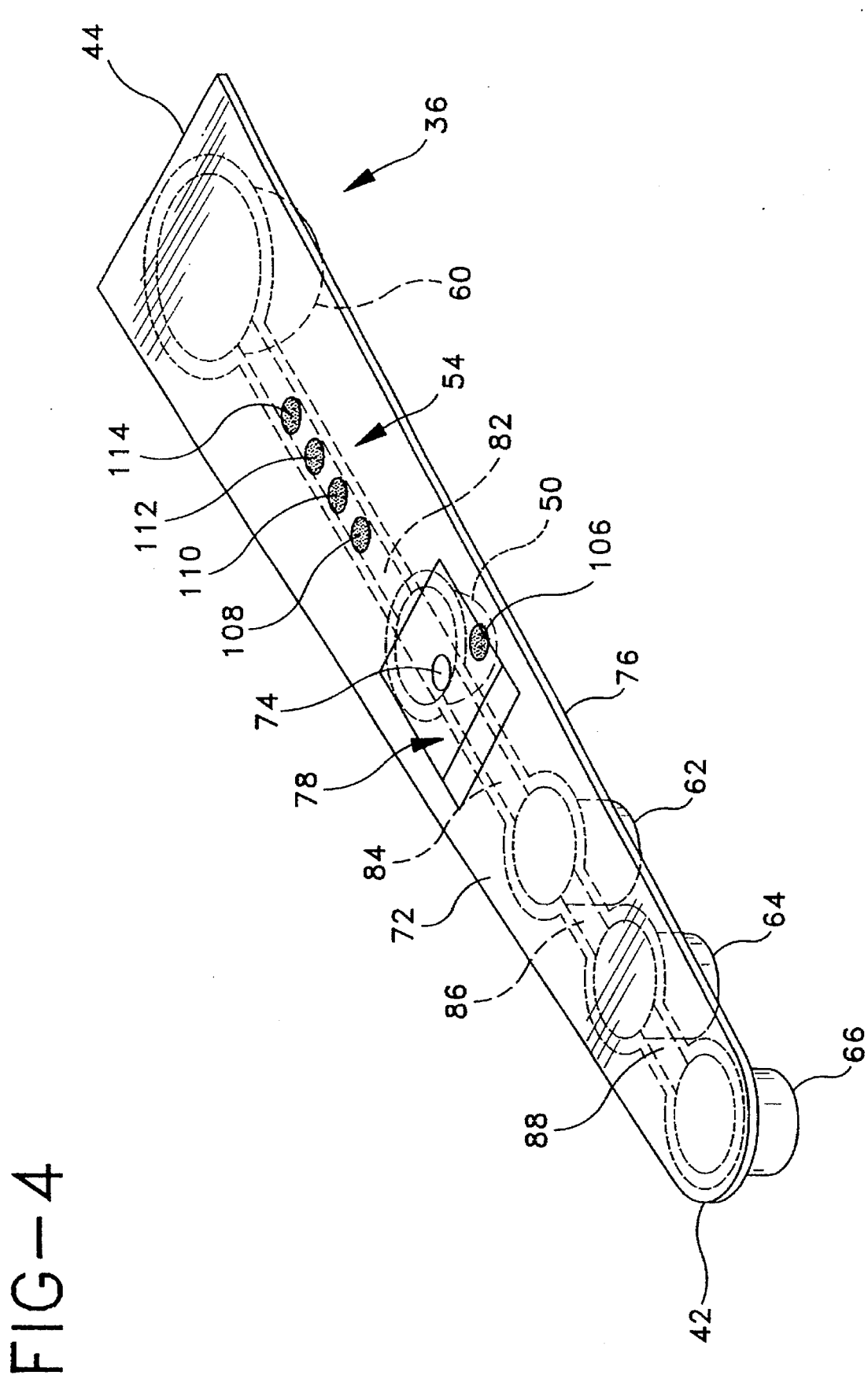
FIG. 4 is an enlarged perspective view illustrating one of the disposable test units used in the instrument of FIG. 1.

The construction of one of the disposable test units will be evident from the perspective view of FIG. 4, the exploded view of FIG. 5, and the plan and side views, respectively, of FIGS. 6A and 6B. Referring first to FIGS. 4 and 5, there are three elements which make up the basic structure of the disposable test unit 36. First, a thin, flexible top film 72, which is preferably made of a transparent or translucent polyester/polyethylene or other heat-sealable laminate approximately 0.005 inch thick, forms the top layer of the test unit 36. This top film 72 has a small hole 74 approximately 0.1 inch in diameter which serves as a sample port. The test unit also includes a thicker, rigid thermoformed bottom portion 76, preferably also transparent or translucent, containing thermoformed depressions or wells 50, 60, 62, 64 and 66. The profile of these wells, which form closed chambers when the top film 72 is in place, can be seen in the side view of FIG. 6B. The depth of the wells preferably varies from about 0.150 inch for the sample chamber 50 to about 0.250 inch for the waste chamber 60. The thermoformed bottom portion 76 is preferably made of a rigid polycarbonate film having a thickness of 0.007 to 0.015 inch, although other heat-resistant rigid plastic films (such as PET-G) can be used if desired. The test unit also includes an adhesive seal 78 which serves as a closure device for the sample port 74. The adhesive seal 78 is made of a polyester film laminated with a downwardly-facing pressure-sensitive adhesive, and is positioned over the sample port 74 during manufacture to serve as a closure device therefor. The top film 72 of the test unit 36 is heat-sealed to the thermoformed bottom portion 76 in order to complete the test unit structure. The heat seal pattern 80 between the top film 72 and thermoformed bottom portion 76 is indicated by stippling in FIG. 6A, and will be seen to define a series of channels 82, 84, 86 and 88 which interconnect the chambers formed by the wells 50, 60, 62, 64 and 66. These channels have widths and lengths as defined by the heat sealing pattern, but the height dimension of each channel is essentially zero since there is no spacer element between the top film 72 and thermoformed bottom 76 during the heat sealing operation. This provides a degree of flow resistance which allows the channels to control the flow of liquids between the various chambers, as will be discussed in more detail shortly. It will be observed that the heat sealing step serves to simultaneously join the top film 72 to the bottom portion 76, and to form the channels 82, 84, 86 and 88. A conventional heated platen, shaped to match the desired heat seal pattern 80, can be used to carry out the heat sealing step.

The assembled test unit 36 is illustrated in FIGS. 7A and 7B with the adhesive seal 78 shown in the open position, and with the reagent chambers 62, 64 and 66 shown pre-filled with liquid reagents. A narrow section 90 of the adhesive seal 78 is bonded, heat-sealed or otherwise affixed to the top film 72 of the test unit 36. The remaining portion of the adhesive seal 78 comprises a flap 92 which is joined to the bonded section 90 by a fold line 94, and which carries a pressure sensitive adhesive (not shown) on its lower surface 96. When the flap 92 is rotated about the fold line 94 in the direction indicated by the arrow 98, the flap 92 becomes adhesively bonded to the top film 72 and thereby closes off the sample port 74. This allows the test unit 36 to be sealed with respect to the outside environment after a liquid biological sample has been introduced into the sample port 74. If desired, a removable release layer (not shown) can be provided on the bottom surface 96 of the flap 92 to prevent the flap 92 from becoming inadvertently attached to the top film 72 before the liquid biological sample has been introduced.

FIGS. 8A and 8B illustrate the test unit 36 after a liquid biological sample has been introduced into the sample chamber 50 through the sample port 74. The adhesive seal 78 is shown in the closed position, thereby sealing the liquid biological sample in the sample chamber 50 and preventing contamination of the surrounding environment. In operation, the adhesive seal 78 is automatically closed by the rotating clamp 40 of FIGS. 1 and 3 when the lid 32 of the test instrument 30 is closed. This saves a considerable amount of time when a number of test units are being processed simultaneously, since the human operator is not required to seal each test unit individually. The automatic sealing feature is also important from the standpoint of avoiding contamination, since the closing of the lid 32 will positively ensure that all test units are properly sealed before the assays are carried out.

FIGS. 9A and 9B are detailed plan and side sectional views, respectively, illustrating the disposable test unit 36 as it might appear prior to the start of a clinical diagnostic assay. The sample chamber 50, which is shown empty in FIGS. 9A and 9B, is connected by means of the channel 82 to the chamber 60, which serves as a waste chamber for receiving the liquid biological sample and liquid reagents used during the assay. The sample chamber 50 is also connected by means of the channel 84 to the chamber 62, which serves as a reagent chamber for containing a first liquid reagent 100. The channel 86 connects the first reagent chamber 62 to the chamber 64, which serves as a second reagent chamber for containing a second liquid reagent 102. Finally, the channel 88 connects the chamber 64 to the chamber 66, which serves as a third reagent chamber for containing a third liquid reagent 104. Typically, the reagent chambers 62, 64 and 66 will be pre-filled with the respective liquid reagents 100, 102 and 104 before the top film 72 of the test unit is heat-sealed to the bottom portion 76. Thus, all of the reagent chambers 62, 64 and 66 are sealed with respect to the surrounding environment, and the same is true of the waste chamber 60. This leaves the sample port 74 as the sole means of fluid communication between the exterior and interior of the test unit 36.

When the test unit is adapted for carrying out an integrated nucleic acid amplification and nucleic acid assay, a dried spot 106 of chemical reagents is affixed to the bottom of the sample chamber 50. This dried spot contains all of the various reagents necessary for nucleic acid amplification, examples of such reagents being disclosed in the above-identified co-pending U.S. patent application or Hugh V. Cottingham entitled "Nucleic Acid Amplification Method and Apparatus". When the test unit 36 is intended for an immunoassay or nucleic acid ligand based assay, the dried spot 106 can contain other reagents or may be deleted. The chemical reagents in the dried spot 106 are carried in a readily soluble matrix, such as trehalose or another carbohydrate. These reagents will spontaneously re-suspend when exposed to an aqueous sample introduced into the sample chamber 50, and are not in any way immobilized. By contrast, dried and immobilized nucleic acid probes and controls are provided at fixed locations in the channel 82 in the form of spots 108, 110, 112 and 114. In the case of an immunoassay, the spots will comprise antibody/antigen and controls, while in the case of a nucleic acid ligand based assay, the spots will comprise nucleic acid ligand/target and controls. In all cases, the immobilized spots are different from the dried reagents 106 in that they are not solubilized by the aqueous sample in the sample chamber 50, and are intended to react with and capture (and thereby also immobilize) a specific chemical moiety in the liquid biological sample if it is present.

Typical antibody/antigen and controls for use in the spots 108, 110, 112 and 114 in immunoassays are well known to those skilled in the art and are described for example in such references as the *Encyclopedia of Immunology*, Academic Press, Ed., Roitt, I. M. and Delves, P. J., volume 2, pages 779-782 (1992) and *Diagnostic Microbiology*, 6th edition, Finegold, S. M. and Martin, W. J., pages 571-583 (1982). Similarly, nucleic acid ligands, which are well known to those skilled in the art through, for example, U.S. Pat. No. 5,270,163, may be used in place of antibodies in well-known immunoassay formats.

In combination with other reagents to be described shortly, the immobilized nucleic acid probes and controls (or, alternatively, antibody/antigen and controls or nucleic acid ligand/target and controls) 108, 110, 112 and 114 generate either a chromogenic, fluorescent, chemiluminescent or bioluminescent response that is suitable for optical detection. Radioactive detection methods may also be used in the practice of the present invention. Preferably, the immobilized spots 108, 110, 112 and 114 are all chemically different from each other, so that each spot detects a different analyte. This allows the test unit 36 to carry out simultaneous multiplexed assays on the same liquid biological sample. The zone 54 occupied by the spots 108, 110, 112 and 114 constitutes the detection site of the test unit 36, and in the illustrated embodiment this detection site simply comprises a portion of the channel 82. In other embodiments, the detection site 54 may comprise a separate chamber or an enlarged section of the channel 82.

The liquid reagent 100 contained in the first reagent chamber 62 is typically an enzyme conjugated to a nucleic acid probe (alternatively, the enzyme is conjugated to an antigen or antibody in the case of an immunoassay, or to a nucleic acid ligand or target in the case of a nucleic acid ligand based assay). The enzyme is typically alkaline phosphatase, horseradish peroxidase, or the like. The liquid reagent 102 in the second reagent chamber 64 is typically an aqueous buffer/wash solution. Finally, the liquid reagent 104 in the third reagent chamber 66 is typically a substrate such as AEC, TMB, BCIP/NBT, AMPPD, BBTP or Lumiphos 530™ for the enzyme in the liquid reagent 100. Other configurations are possible; for example, a liposome detector and wash may be used, and this will require one less reagent chamber and liquid reagent.

By virtue of the linear arrangement of the chambers 50, 60, 62, 64 and 66 and interconnecting channels 82, 84, 86 and 88, centrifugal force can be applied by the apparatus of FIGS. 1-3 to properly sequence the flow of the liquid biological sample and liquid reagents through the test unit 36. Centrifugal force is defined by the relationship:

$$C_f = mr\omega^2$$

where:

$C_f$=centrifugal force m=mass r=radius of revolution

ω=angular velocity

Although centrifugal analyzers are well known in clinical chemistry, these devices typically use centrifugal force to mix different reagents. In the illustrated embodiment of the present invention, mixing occurs only incidentally (in the waste chamber 60) and the centrifugal force serves primarily to sequentially move the liquid biological sample and liquid reagents across the immobilized reagent spots 108, 110, 112 and 114 by overcoming the flow resistance of each of the channels 82, 84, 86 and 88 in turn. This is possible since the chambers 50, 62, 64 and 66 are located at progressively decreasing radial distances from the axis of the rotor 34 in FIGS. 1-3, with the waste chamber 60 being located at the outermost radial position so that it can receive liquids from all of the other chambers. In the preferred embodiment, the center of the third reagent chamber 66 has a radius of revolution of about 1.1 inches, the center of the second reagent chamber 64 has a radius of revolution of about 1.6 inches, the center of the first reagent chamber 62 has a radius of revolution of about 2.1 inches, and the center of the sample chamber 50 has a radius of revolution of about 2.85 inches. For a given angular velocity, this results in a greater centrifugal force being exerted on the liquid in each chamber as the radius of revolution increases. Accordingly, for a given angular velocity, the sample chamber 50 would have the most force exerted on its contents, the first reagent chamber 62 would have a somewhat smaller force exerted on its contents, the second reagent chamber 64 would have a still smaller force exerted on its contents, and the third reagent chamber 66 will have an even smaller force exerted on its contents. Numerically, the force exerted on the contents of the first reagent chamber 62 will be 73% of the force exerted on the contents of the sample chamber 50, the force exerted on the contents of the second reagent chamber 64 will be 56% of the force exerted on the contents of the sample chamber 50, and the force exerted on the contents of the third reagent chamber 66 will be 38% of the force exerted on the contents of the sample chamber 50. Conversely, to achieve the same given force on the contents of all chambers, the angular velocity of the first reagent chamber 62 would have to be 116% of the angular velocity of the sample chamber 50, the angular velocity of the second reagent chamber 64 would have to be 133% of the angular velocity of the angular velocity of the sample chamber 50, and the angular velocity of the third reagent chamber 66 would have to be 160% of the angular velocity of the sample chamber 50.

Figure 10C:
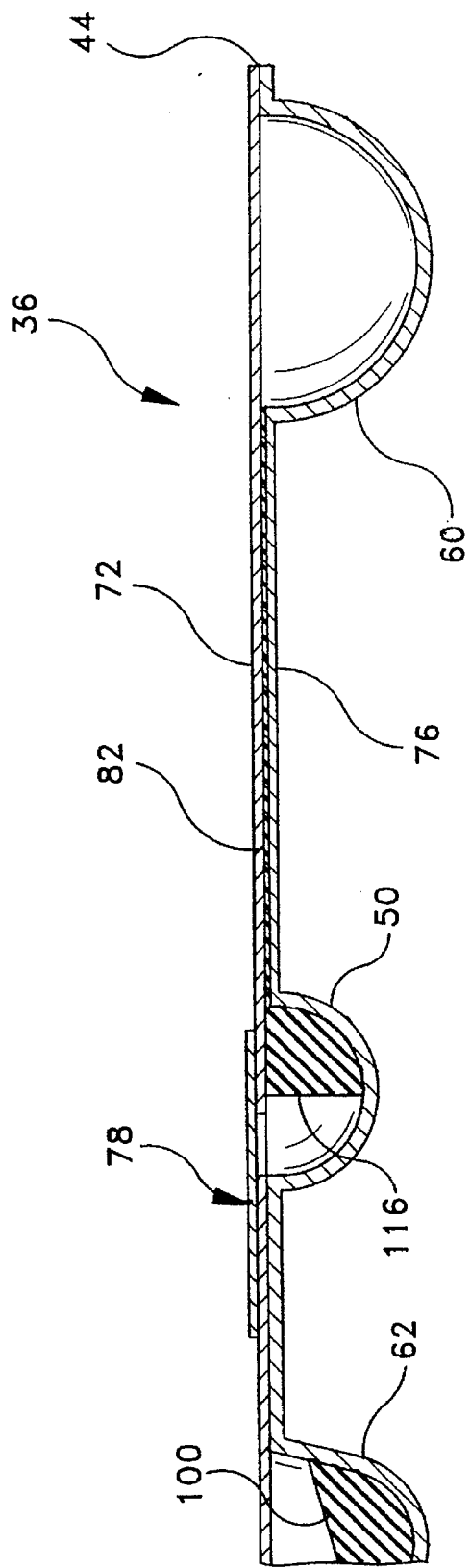

FIGS. 10A, 10B and 10C illustrate the disposable test unit 36 after a liquid biological sample 116 has been introduced into the sample chamber 50 and the sample has begun to be assayed. Assuming that an integrated nucleic acid amplification and nucleic acid assay is being carried out, the dried reagent spot 106 in the sample chamber has already dissolved at this point and nucleic acid amplification has occurred in the liquid biological sample 116. The test unit 36 has been placed into its assigned radial position on the rotor 34 of the apparatus 30 in FIGS. 1–3, and the test unit 36 is being rotated at a threshold angular velocity that is sufficient to force the liquid sample 116 radially outward. The channel 82, which is normally closed by virtue of its upper wall being resiliently held in contact with its lower wall, is forced open by the radial pressure exerted on the liquid sample 116. This is illustrated in FIG. 10C. Depending upon the thickness and resiliency of the materials used for the top film 72 and bottom portion 76 of the test unit 36, the opening of the channel 82 may result from the deflection of either the top or bottom wall of the channel, or both. In the illustrated embodiment, the deflection is relatively small (on the order of 50 microns) and occurs primarily in the top wall of the channel since the top film 72 of the test unit 36 is thinner and more flexible than the bottom portion 76. The opening of the channel 82 allows the liquid biological sample 116 to flow over the immobilized reagent spots 108, 110, 112 and 114 and to react with the immobilized reagents at these locations. The liquid biological sample 116 continues to flow out of the sample chamber 50, through the channel 82 and into the waste chamber 60, until the sample chamber 50 is empty. When the flow stops, none of the liquid biological sample 116 remains in either the sample chamber 50 or in the channel 82, and the waste chamber 60 is partially filled. It will be noted that, while the amount of centrifugal force being exerted on the liquid biological sample 116 in FIGS. 10A through 10C is sufficient to cause the sample 116 to flow through the channel 82, it is not sufficient to cause any of the liquid reagents 100, 102 and 104 to force open their respective channels 84, 86 and 88. This may result from the fact that the top surfaces of the liquid reagents 100, 102 and 104 have not yet tilted sufficiently to reach the level of the channel openings in the respective wells 62, 64 and 66, as suggested in FIGS. 10A through 10C, or from the fact the reagents, although having reached the channel openings, are not yet under sufficient pressure to force open the resilient walls of the channels. Either or both of these effects may be relied upon in the practice of the present invention. In any event, to allow the liquid reagents 100, 102 and 104 to flow out of their respective chambers, the angular velocity of the rotor 34 in FIGS. 1–3 must be increased. Until this occurs, the channels 84, 86 and 88 remain closed and effectively seal off the respective reagent chambers 62, 64 and 66 from each other and from the sample chamber 50.

FIGS. 11A and 11B illustrate the test unit 36 at a second threshold angular velocity that is higher than the angular velocity represented in FIGS. 10A and 10B. This higher angular velocity is sufficient to force the liquid reagent 100 in the first reagent chamber 62 radially outward into the channel 84. This allows the liquid reagent 100 to flow through the channel 84 to the sample chamber 50, and from the sample chamber 50 through the channel 82 to the waste chamber 60. In flowing through the channel 82, the liquid reagent 100 flows over the immobilized reagent spots 108, 110, 112 and 114 and reacts with the immobilized reagents therein. The flow of the liquid reagent 100 continues until the reagent chamber 62 and channels 82 and 84 are empty, and the liquid reagent 100 has been received completely in the waste chamber 60. It should be noted that, as a result of the relatively high magnitude of the centrifugal force applied to the liquid reagent 100 as compared to the force of gravity, the liquid reagent does not accumulate to any appreciable extent in the sample chamber 50 as it flows from the channel 84 to the channel 82. Instead, the liquid reagent 100 flows primarily across the top of the sample chamber 50 between the outlet of the channel 84 and inlet of the channel 82. As before, the centrifugal force exerted on the liquid reagent 100 in FIGS. 11A and 11B is sufficient to cause the reagent 100 to flow through the channels 84 and 82, but is not sufficient to allow the liquid reagents 102 and 104 in the remaining reagent chambers 64 and 66 to overcome the flow resistance of their respective channels 86 and 88. In order for the liquid reagents 102 and 104 to begin to flow, the angular velocity must be increased still further to increase the centrifugal force at these locations.

FIGS. 12A and 12B illustrate the test unit 36 at a third threshold angular velocity that is higher than the angular velocity represented in FIGS. 11A and 11B. At this angular velocity, the centrifugal force exerted on the liquid reagent 102 in the second reagent chamber 64 is sufficient to overcome the flow resistance exerted by the channel 86 and allow the reagent 102 to flow through the channel 86. Accordingly, the reagent 102 flows to the waste chamber 60 via the channel 86, first reagent chamber 62, channel 84, sample chamber 50 and channel 82. In flowing through the channel 82, the liquid reagent 102 flows over the immobilized reagent spots 108, 110, 112 and 114 and reacts with the immobilized reagents therein. The liquid reagent 102 continues to flow until the second reagent chamber 64 is empty and all of the reagent 102 has accumulated in the waste chamber 60. As before, the centrifugal force exerted upon the liquid reagent 102 in FIGS. 12A and 12B is sufficient to cause the reagent 102 to flow through the channels 86, 84 and 82, but is not sufficient to allow the liquid reagent 104 in the third reagent chamber 66 to overcome the flow resistance exerted by the channel 88. In order to allow the liquid reagent 104 to flow into the channel 88, the angular velocity must again be increased to further increase the centrifugal force at the location of the third reagent chamber 66.

FIGS. 13A and 13B illustrate the disposable test unit 36 at a fourth threshold angular velocity that is higher than the angular velocity represented in FIGS. 12A ad 12B. At this angular velocity, the centrifugal force exerted on the liquid reagent 104 in the third reagent chamber 66 is sufficient to force open the channel 88 and allow the reagent 104 to flow through the channel 88. This allows the liquid reagent 104 to flow into the waste chamber 60 via the channel 88, second reagent chamber 64, channel 86, first reagent chamber 62, channel 84, sample chamber 50 and channel 82. In flowing through the channel 82, the liquid reagent 104 flows over the immobilized reagent spots 108, 110, 112 and 114 and reacts with the immobilized reagents in these spots. The liquid reagent 104 continues to flow into the waste chamber 60 until the third reagent chamber 66, and all of the intervening channels and reagent chambers, are empty. At this point, all of the liquid reagent 104 has accumulated in the waste chamber 60, along with the liquid biological sample 116 and the first and second liquid reagents 100 and 102.

FIGS. 14A and 14B illustrate the state of the disposable test unit 36 after the liquid biological sample 116 and all of the liquid reagents 100, 102 and 104 have been forced through the channels and into the waste chamber 60. The immobilized reagent spots 108, 110, 112 and 114 have now been exposed to the liquid biological sample 116 and to each of the assay reagents 100, 102 and 104. The order of exposure, and hence the order of reaction, has been controlled by the increasing centrifugal forces generated by the increasing angular velocities of the rotor 34 in the apparatus 30 of FIGS. 1-3. As will be appreciated from the foregoing description, this order is as follows: first, the liquid biological sample 116; second, the enzyme conjugate 100; third, the wash solution 102; and fourth, the substrate 104. At this point, the immobilized reagent spots 108, 110, 112 and 114 are ready to be optically detected. Depending upon the substrate used, the immobilized reagent spots will exhibit either color development, fluorescence or luminescence proportional to the amount of the particular analyte detected.

Figure 15:
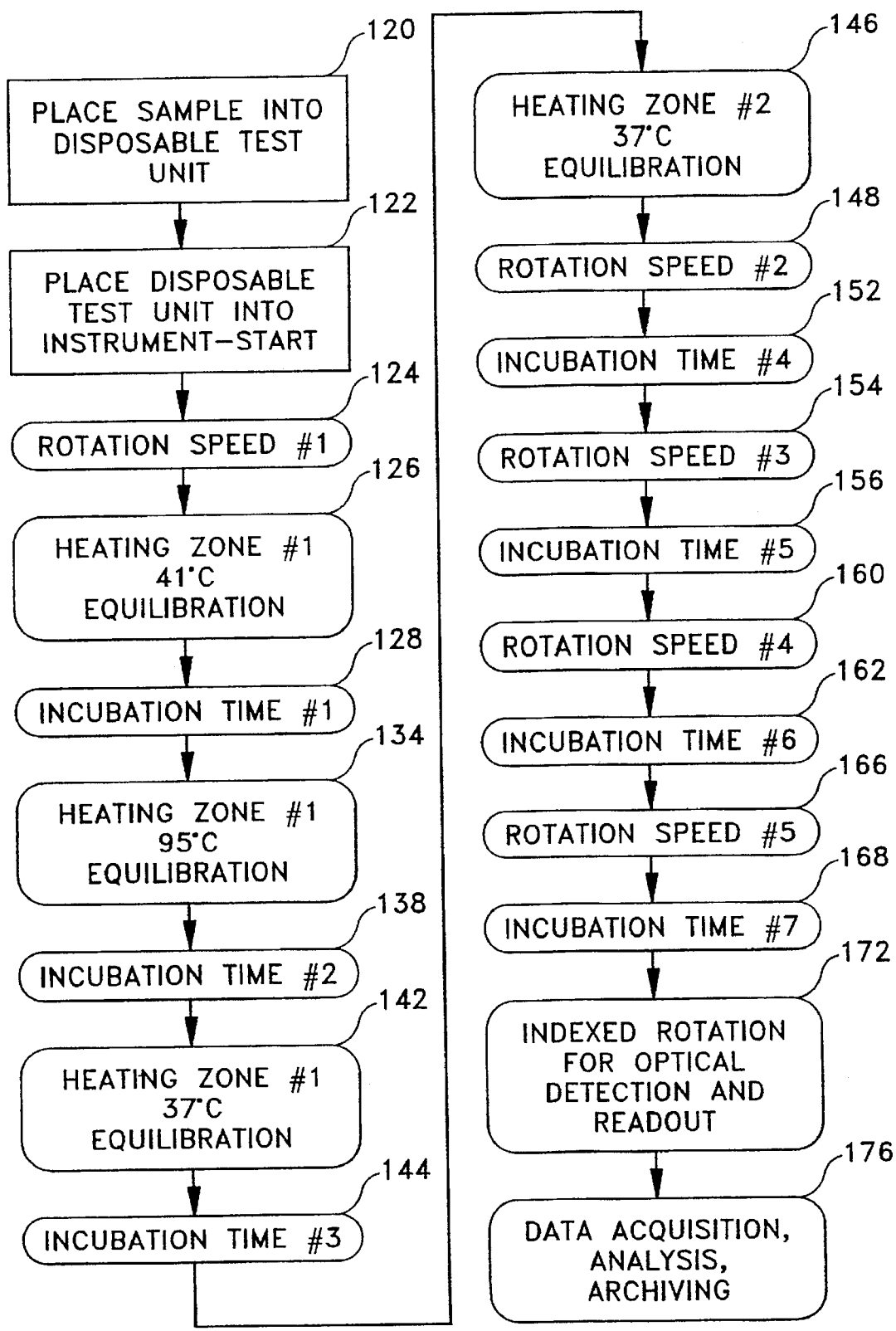
FIG. 15 is a flow chart of the steps involved in carrying out an integrated nucleic acid amplification and nucleic acid assay using the automated test instrument of FIG. 1 and the disposable test unit of FIG. 4.
Figure 16:
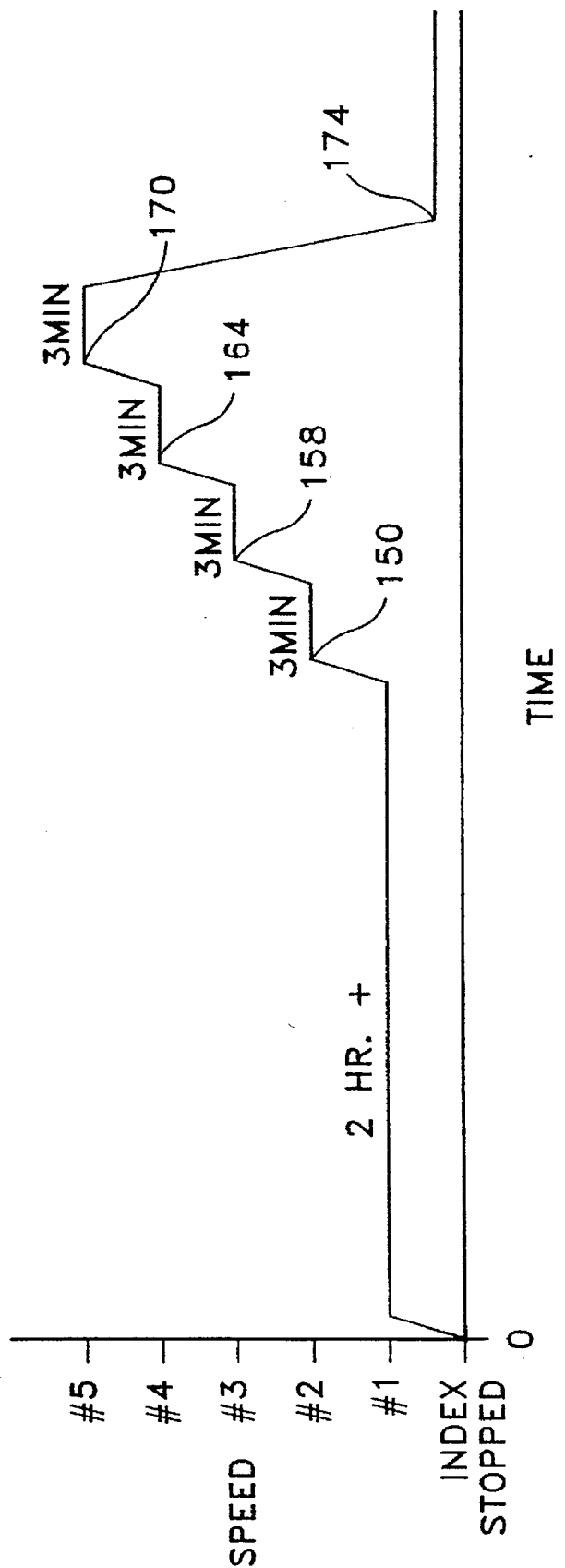
FIGS. 16A and 16B are graphs illustrating the manner in which the rotational speed and temperature of the disposable test units are varied over time during an integrated nucleic acid amplification and nucleic acid assay, using the automated test instrument of FIG. 1.

FIG. 15 is a flow chart which summarizes the series of operations carried out by the operator and by the test instrument 30 of FIGS. 1-3 during an integrated nucleic acid amplification and nucleic acid assay. FIGS. 16A and 16B are graphs of rotational speed versus time and temperature versus time, respectively, which will assist in the understanding of the flow chart of FIG. 15. With reference to block 120 of FIG. 15, the process is initiated by the human operator by placing a liquid biological sample into the sample chamber 50 of the disposable test unit 36 through the sample port 74. In block 122, the disposable test unit 36 is placed into its assigned radial position on the rotor 34 of the apparatus 30 (along with any other test units 36 that are to be assayed), and the lid 32 is closed to seal the test units and hold them in position. A start command is also applied, either automatically by closing the lid 32 or by depressing a separate pushbutton (not shown). Optionally, the rotor 34 of the apparatus 30 may have temperature cycling capability in order to accommodate the polymerase chain reaction (PCR) nucleic acid amplification process. This is the end of any required action by the human operator, and all subsequent steps in the process are fully automated. It should be noted that the liquid biological sample may be placed into the test unit sample chamber 50 either before or after the test unit is placed in the rotor 34, depending upon the preference of the operator.

Blocks 124 through 144 of FIG. 15 are associated with the nucleic acid amplification. In block 124, the rotor 34 is rotated at a speed of a few revolutions per minute (RPM) for the purpose of uniformly heating all of the liquid biological samples in the sample chambers 50 test units 36 to the same temperature. Rotation eliminates hot or cold spots and averages any local variations in the temperatures of the heaters 48 and 52 across all of the test units 36. In block 126, the infrared heater 48 of FIG. 3 is raised to a temperature sufficient to heat all of the liquid biological samples in the test units 36 to a temperature of 41° C., the temperature necessary for amplification. (The time-temperature profile of the infrared heater 48 corresponds to heating zone 1 in FIG. 16B, and the time-temperature profile of the infrared heater 52 corresponds to heating zone 2.) In block 128, an incubation time is provided for nucleic acid amplification to occur while the samples are maintained at 41° C. Amplification starts at the beginning of the incubation period (point 130 in FIG. 16B) and is terminated approximately two hours later (point 132 in FIG. 16B). In block 134, the infrared heater 48 is controlled to raise the temperature of the liquid biological sample in the test units 36 to 95° C., the temperature necessary to destroy the amplification reagents and terminate the amplification process. This corresponds to point 136 in FIG. 16B. In block 138, a 3-minute incubation time is provided for this destruction to occur. The incubation time ends at point 140 in FIG. 16B, and is followed by a cool-down step in block 142 of FIG. 15. During the cool-down step, the infrared heater 48 is controlled to reduce the temperature of the liquid biological samples in the test units 36 to 37° C. for the assay procedure to follow. In block 144, a suitable incubation time is provided to assure that all of the liquid biological samples have an opportunity to stabilize at the same lower temperature. This marks the end of the amplification procedure, and the nucleic acid assay follows.

In block 146, the nucleic acid assay begins with a heating step in which the infrared heater 52 of FIG. 3 is controlled to raise the temperature of the detection sites 54 of the disposable test units to 37° C., the desired assay temperature. In block 148, the rotational speed of the rotor 34 is increased to a first threshold speed which is sufficient to force the liquid biological samples to move out of the sample chambers 50 of the test units 36 and through the channels 82 toward the waste chamber 60. Block 148 corresponds to point 150 in FIG. 16A. In block 152, this rotational speed is maintained for a sufficient period of time (typically about three minutes) to allow all of the liquid biological sample to flow from the sample chamber 50 to the waste chamber 60. During this period, the liquid biological sample flows past the immobilized reagent spots 108, 110, 112 and 114 in the channel 82, and reacts with the reagents contained in these spots. In blocks 154 and 156, the rotational speed of the rotor 34 is increased to a second threshold level (point 158 in FIG. 16A) which is sufficient to cause the enzyme 100 to flow out of the first reagent chamber 62 of each test unit 36, and is maintained at this rotational speed for a further period of time (typically about three minutes). This allows sufficient time for the enzyme 100 to flow completely out of the first reagent chamber 62, past the immobilized reagent spots 108, 110, 112 and 114, and into the waste chamber 60. In blocks 160 and 162, the rotational speed of the rotor 34 is increased to a third threshold level (point 164 in FIG. 16A) which is sufficient to cause the aqueous buffer/wash solution 102 to flow out of the second reagent chamber 64, and is maintained at that level for an additional period of time (typically about three minutes). The period chosen is sufficient to allow the aqueous buffer/wash solution 102 to flow completely out of the second reagent chamber 64, past the immobilized reagent spots 108, 110, 112 and 114, and into the waste chamber 60. Finally, in blocks 166 and 168, the rotational speed of the rotor 34 is increased to a fourth threshold level (point 170 in FIG. 16A) which is sufficient to force the substrate 104 to flow out of the third reagent chamber 66, and is maintained at that level for a further period of time (typically about three minutes). As before, this interval is sufficient to allow the substrate to flow completely out of the third reagent chamber 66, past the immobilized reagent spots 108, 110, 112 and 114 and into the waste chamber 60. At this point, the liquid biological sample 116 and liquid reagents 100, 102 and 104 have all been sequenced, one at a time, past the immobilized reagent spots 108, 110, 112 and 114 by virtue of the progressively increasing speed of rotation of the rotor 34. The nucleic acid assay is now complete, except for detection. In block 172, the detection operation is carried out by slowing the rotor 34 to an indexing speed (point 174 in FIG. 16A) and using the optical detector assembly 68 to illuminate and detect the immobilized reagent spots 108, 110, 112 and 114 in each of the disposable test units 36. Depending upon the particular substrate used, the immobilized reagent spots 108, 110, 112 and 114 will be either chromogenic, fluorescent, luminescent or, as noted earlier, radioactive. It will be appreciated that the indexing speed of the rotor 34 represented by point 174 in FIG. 16A may either be constant or intermittent, depending upon whether the optical detector assembly 68 requires that the test units 36 be stopped in order to properly detect the immobilized reagent spots 108, 110, 112 and 114. The optical detector assembly 70 of FIG. 3 indicates the position of each test unit 36 on the rotor 34 and, in the case where the rotor 34 must be stopped for detection, also indicates the proper stopped positions of the rotor 34. The nucleic acid assay procedure concludes in block 176, where data obtained from the optical assembly 68 for each of the test units 36 is acquired, analyzed and archived by a computer-based control system.

Figure 17:
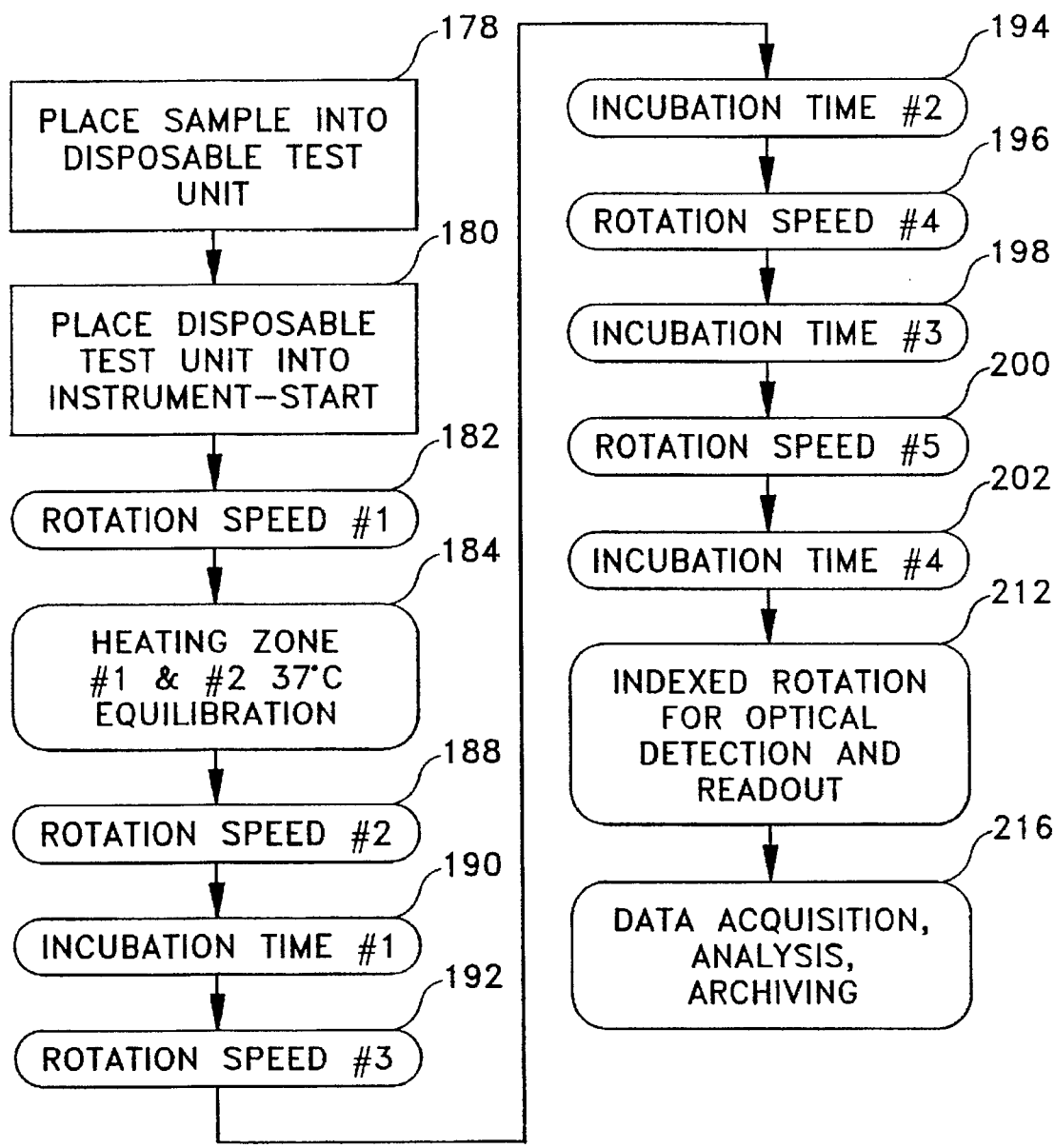
FIG. 17 is a flow chart of the steps involved in carrying out an immunoassay or nucleic acid ligand based assay using the automated test instrument of FIG. 1 and the disposable test unit of FIG. 4.
Figure 18B:
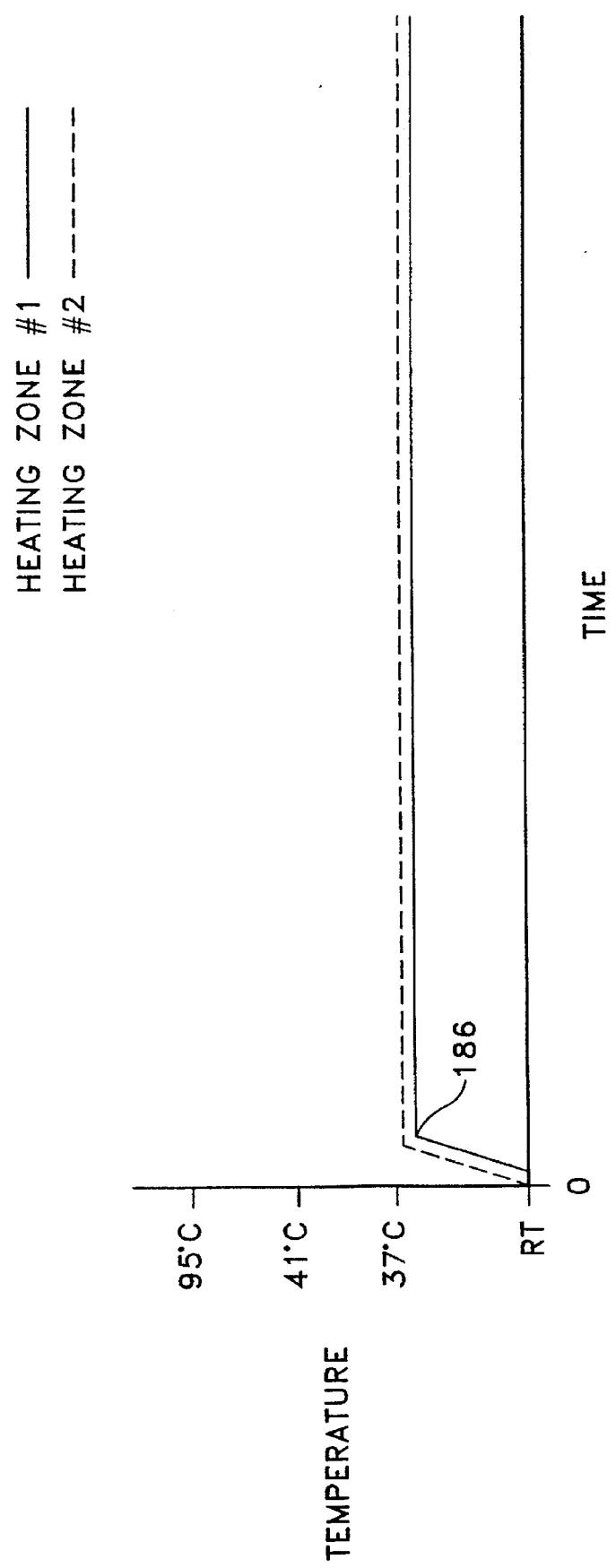

FIG. 17 is a flow chart which summarizes the series of operations carried out by the operator and by the apparatus 30 of FIGS. 1–3 during an immunoassay or nucleic acid ligand based assay. FIGS. 18A and 18B are graphs of rotational speed versus time and temperature versus time, respectively, which will assist in the understanding of the flow chart of FIG. 17. In blocks 178, 180 and 182 of FIG. 17, the immunoassay or nucleic acid ligand based assay procedure is commenced using the same steps as those described in connection with blocks 120, 122 and 124 of FIG. 15. In block 184, both of the infrared heaters 48 and 52 of FIG. 3 are controlled to heat the sample chambers 50 and detection sites 54 of the disposable test units 36 to the desired immunoassay or nucleic acid ligand based assay temperature of 37° C. This is indicated by point 186 in FIG. 18B. After a short period of equilibration, the rotational speed of the rotor 34 is sequenced through four progressively increasing threshold levels, each followed by a three-minute incubation period. This sequence of events is represented by blocks 188, 190, 192, 194, 196, 198, 200 and 202 in FIG. 17, which correspond, respectively, to blocks 148, 152, 154, 156, 160, 162, 166 and 168 of FIG. 15. The rotational speeds of the rotor 34 in blocks 188, 192, 196 and 200 of FIG. 17 are represented by the points 204, 206, 208 and 210, respectively, of FIG. 18A. In block 212 of FIG. 17 (corresponding to point 214 of FIG. 18A), indexed rotation of the rotor 34 takes place to allow detection of the immobilized reagent spots 108, 110, 112 and 114 by the optical assembly 68 of FIG. 3. This step is equivalent to that represented by block 172 in FIG. 15. In block 216 of FIG. 17, data acquisition, analysis and archiving is carried out by the computer-based control system as described previously in connection with block 176 of FIG. 15. The assay is then complete. It will be observed that the immunoassay or nucleic acid ligand based assay procedure of FIGS. 17, 18A and 18B is similar to the nucleic acid amplification and assay procedure described previously in connection with FIGS. 15, 16A and 16B, except that the immunoassay or nucleic acid ligand based assay does not require the two-hour incubation period used for nucleic acid amplification, nor the 41° C. and 95° C. heating steps.

FIG. 19 illustrates the manner in which two or more of the automated test instruments 30 of FIGS. 1–3 may be connected to a single host computer 218. The host computer receives test results and other data from the internal microcontroller boards 46 of the test instruments 30, and serves as a gateway for making this data available to other computers 220, 222 and 224 on a local area network (LAN) 226 within a hospital or clinical laboratory. The host computer 218 may be one of the computers on the LAN 226, or it may be a separate computer which connects to the LAN 226 by means of a standard network interface such as Ethernet. By distributing the system in this way, the test instruments 30 can be operated essentially in the same manner as computer peripheral devices for carrying out data acquisition, and the assay results can be made generally available throughout the organization served by the LAN. Support for database operations, display and printing can be provided by hardware already connected to the LAN 226, which reduces the need for dedicated hardware. Hospitals, in particular, often have a mix of mainframe computers, personal computers linked by local area networks, fiber optic networks, and so on. It is desirable to be able to place a new instrument on line without substantially affecting existing hardware and software, in order to minimize the installation cost of the new instrument. In the case of the test instrument 30, this is achieved by having the internal microcontroller board 46 run the instrument 30, so that the computational overhead of the host computer 218 is reduced to the point where it can run the test instrument 30 in the background. Moreover, by utilizing existing standardized hardware and software for display, printing, data distribution and archiving, the manufacturing cost of the test instrument 30 itself is reduced, and the cost of installing and maintaining the instrument 30 is also reduced.

Figure 20:
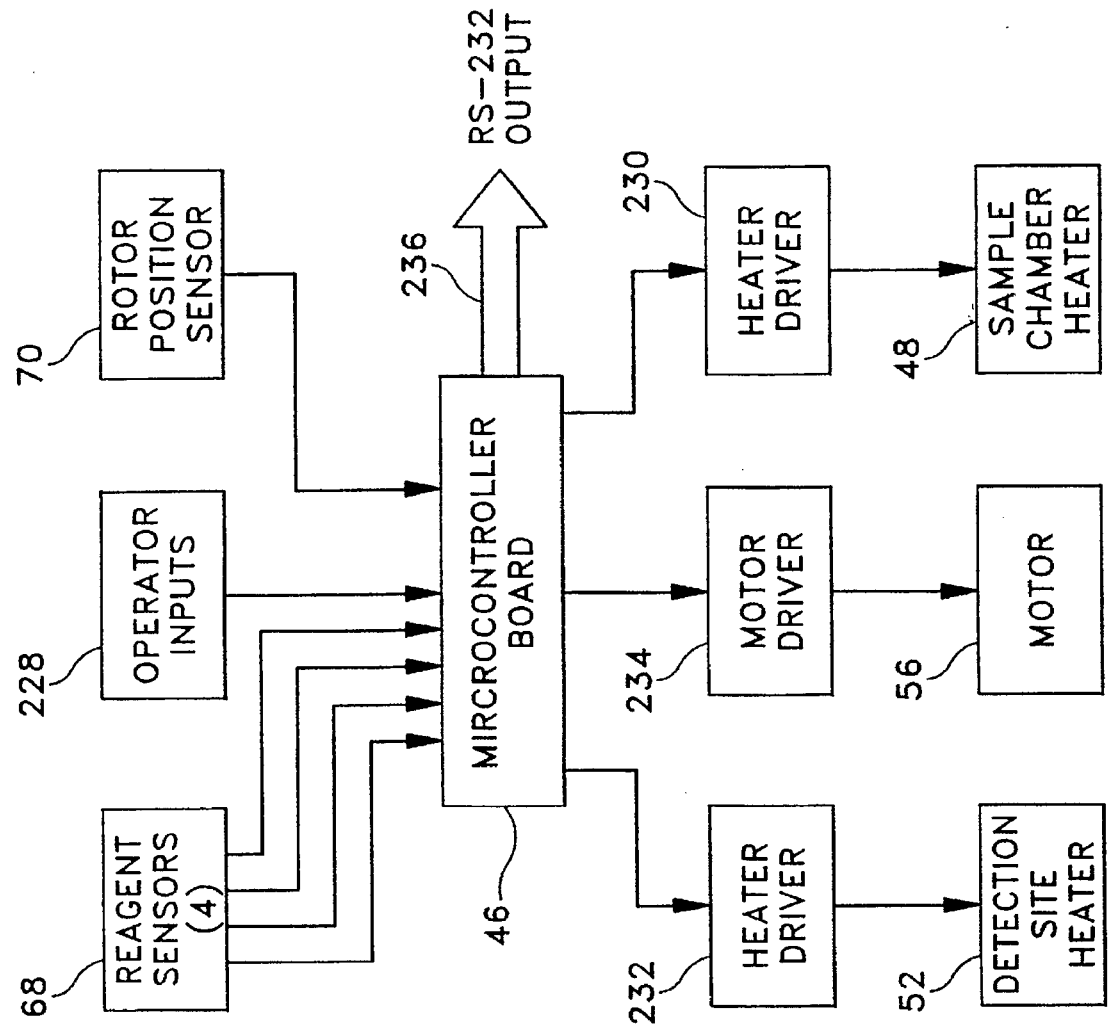
FIG. 20 is a block diagram of the principal electrical components used in the automated test instrument of FIG. 1.

FIG. 20 is a block diagram illustrating the principal electrical components of the automated test instrument 30 of FIGS. 1–3. The microcontroller board 46 controls the operations of the test instrument 30 and contains a microprocessor, read-only memory (ROM) for storing program code, and random access memory (RAM) for storing assay results and computational data during operation of the test instrument 30. The microcontroller board 46 received inputs from the first and second optical assemblies 68 and 70 of FIGS. 2 and 3. These inputs provide data relating to assay test results and the rotational position of the rotor 34. The microprocessor also receives operator inputs from one or more external input devices 228, which may consist of "start" and "stop" pushbuttons, a sensor for detecting when the lid 32 is closed, and so on. The outputs of the microcontroller board 46 are connected to the infrared heaters 48 and 52 and to the motor 56 through respective driver circuits 230, 232 and 234. The driver circuits provide appropriate interfacing, isolation and current drive for the heaters 48, 52 and motor 56, respectively. Depending upon the type of motor 56 used, the motor driver circuit 234 may include servo control circuits for operating the motor at precise speeds and/or for indexing the motor between precise rotational positions. If a stepper motor is used for the motor 56, a known type of stepper motor drive circuit may be employed for the driver circuit 234. The optical sensor 70 used for detecting the rotational position of the rotor 34 may, if desired, be replaced with a shaft encoder coupled to the shaft 58 of the motor 36 or to the rotor 34. The output 236 of the microcontroller board is preferably a standard interface, such as an RS-232 interface, which can be connected directly to the host computer 218 of FIG. 19. FIGS. 21A and 21B are enlarged plan and side sectional views, respectively, of a modified embodiment 36' of the disposable test unit 36 described previously. In the modified embodiment, the sample chamber 50', waste chamber 60' and reagent chambers 62', 64' and 66' are generally in the same positions as described earlier, and the immobilized reagent spots 108', 110', 112' and 114' are disposed in the channel 82' connecting the sample chamber 50' and waste chamber 60' as before. In the modified embodiment of FIGS. 21A and 21B, however, the channels 84', 86' and 88' communicating with the respective reagent chambers 62', 64' and 66' lead directly to the inlet of upstream end of the channel 82', without passing through any intermediate chambers or channels. This arrangement may be preferable in that the flow of liquid reagents between the reagent chambers 62', 64' and 66' and the channel 82' is somewhat smoother and less impeded, but it is also more difficult to fabricate because the channels 84', 86' and 88' run parallel to each other for a portion of their length. The modified embodiment illustrates that the channels of the disposable test unit need not follow straight radial lines relative to the axis of rotation of the rotor 34 in order for the liquid sample and reagents to move between the various chambers under the influence of centrifugal force. However, in order to insure optimum liquid flow through each channel, there should preferably be a component of centrifugal force acting in the desired flow direction at each point along the channel. In practice, this means that the channels can have any desired configuration as long as they are non-reversing; that is, when viewed in the intended flow direction, each successive incremental section of the channel should be no closer to the intended axis of rotation (i.e., the axis of the rotor 34 in FIGS. 1–3) than the preceding section. Viewed from the standpoint of the test unit 36 or 36' itself, the channels are non-reversing if it is possible to select at least one axis of rotation of the test unit for which all channels satisfy the previously stated condition. Clearly, there are many different non-reversing channel configurations which can be used in the practice of the present invention.

In a further embodiment of the invention, not illustrated in the drawings, the test unit 36 may comprise top and bottom portions corresponding generally to the portions 72 and 76 in FIGS. 4 and 5, but made from a relatively thick, rigid acrylic material. Rather than using heat sealing to secure the top and bottom portions together and to define the channels, a thin vinyl or polyester/ACLAR/polypropylene membrane is interposed between the top and bottom portions, and the underside of the top portion has a projecting relief pattern which is in the shape of the heat seal pattern 80 of FIG. 6A. When the top and bottom portions are secured together with screws or other suitable fasteners, the membrane provides a seal around the chambers and also defines the interconnecting channels in a manner similar to the heat seal pattern 80. The flexibility of the membrane closes off the channels in the absence of centrifugal force applied by the rotation of the rotor 34 of FIGS. 1–3, in the same manner as the flexible top film 72 in FIGS. 4 and 5. In this embodiment, the immobilized reagent spots 108, 110, 112 and 114 of FIG. 4 are preferably provided on the membrane (or on a nitrocellulose carrier that is affixed to the test unit by two parallel strips of transfer tape aligned in the liquid flow direction) rather than on the acrylic material.

In the embodiment just described, the walls of the sample and reagent chambers may be inclined at a somewhat shallower angle in the regions immediately adjoining the channel entrances, in order to promote the entry of liquid into the channels when the test unit is in use. Preferably, the inclination angle becomes progressively steeper with decreasing distance from the axis of the rotor 34 in FIGS. 1–3; that is, the shallowest angle is used for the sample chamber and the steepest angle is used for the last reagent chamber. This is advantageous in that it tends to widen the differences in the rotational speeds at which the successive chambers will empty of liquids. In one possible implementation, an inclination angle of 30° is used for the sample chamber exit region and inclination angles of 48°, 67° and 85°, respectively, are used for the exit regions of the succeeding reagent chambers. In addition to (or in lieu of) the inclined exit regions, the depth of the chambers may be made successively greater in the direction from the sample chamber radially inward toward the last reagent chamber. By thus requiring the liquids in the successive chambers to climb progressively greater distances to reach the channel entrances, the differences in the rotational speeds needed to empty the successive chambers will again be widened. In one possible implementation, the depth of the sample chamber is 4.4 millimeters and the depths of the succeeding reagent chambers are 7.1 millimeters, 7.7 millimeters and 8.0 millimeter, respectively. It will be appreciated that the use of inclined chamber exit regions and varying chamber depths, although described in connection with the non-illustrated modified embodiment, may also be used in the previously-described embodiments illustrated in FIGS. 1–21.

As another feature of the modified embodiment described above, the channel connecting the sample and waste chambers (corresponding to the channel 82 or 82' in the illustrated embodiment described previously) may be a fixed-dimension channel or capillary which remains open even when centrifugal pressure is not being applied to the liquid in the sample chamber. This is feasible since the sample chamber is normally empty of liquid until just before the test unit is placed into use, and hence there is no risk of liquids inadvertently being caused to flow through the channel during shipping, storage and handling of the test unit prior to use. Even with an open channel, centrifugal force will still be required to cause the liquid sample to flow from the sample chamber to the waste chamber, either because the liquid must incline somewhat to reach the channel entrance or because of the inherent flow resistance of the channel or capillary walls (or for both of these reasons). In some cases, these latter effects may exert sufficient flow control that resiliently constricted channel walls may be omitted from the test unit altogether, even for the channels leading from the reagent chambers. Again, although the use of fixed-dimension channels has been described in connection with the non-illustrated embodiment, it is also applicable to the previously-described embodiments illustrated in FIGS. 1–21.

Other modifications of the embodiments described herein are also possible. For example, two or more parallel channels may be provided between the sample and waste chambers in lieu of the single channel 82 or 82', to facilitate the detection of different antibodies in certain types of immunoassays (e.g., the IGG and IGM antibodies in an assay for Rubella). Alternatively, two or more independent sample chambers and channels may be provided, thereby forming the functional equivalent of two separate test units with common reagent and waste chambers. In any or all of the embodiments described herein, venting may be provided in the various chambers of the test unit to promote liquid flow through the interconnecting channels, but this should be done in such a way that the test unit remains effectively sealed against contamination. Also, it will be apparent that the channels connecting the various chambers can be designed with different flow resistances if desired, and this may make it unnecessary to locate the chambers at different radial distances from the axis of rotation in order to cause the liquid biological sample and liquid reagents to flow sequentially with increasing rotational speed. As a further alternative, the orientation of the test units on the rotor can be changed during the course of the assay, either manually or by a mechanical actuator within the test instrument 30, in order to modify the centrifugal forces applied to the chambers. It will also be appreciated that the constricted channels used in the illustrated embodiments may be replaced with other types of flow control devices if desired, such as valves, weirs, capillaries or the like. Microchannels of the type described in the aforementioned co-pending U.S. patent application of Hugh V. Cottingham, incorporated by reference herein, may also be used for this purpose.

The foregoing is illustrative of the present invention, and is not to be construed as limiting thereof, as numerous alternatives to the devices and methods described which incorporate the present invention will be apparent to those skilled in the art. The invention is accordingly defined by the following claims with equivalence of the claims to be included therein.

That which is claimed is:

1. A test unit for carrying out a clinical diagnostic assay, comprising:

a sample chamber within said test unit for receiving a liquid biological sample to be assayed a waste chamber within said test unit in fluid communication with said sample chamber for receiving said liquid biological sample from said sample chamber;

a first liquid flow path for said liquid biological sample within said test unit communicating between said sample chamber and said waste chamber;

non-frangible flow control means for preventing the flow of said liquid biological sample from said sample chamber to said waste chamber through said first liquid flow path in the absence of a force applied to said sample, and for permitting said liquid biological sample to flow from said sample chamber to said waste chamber through said first liquid flow path when at least a predetermined minimum force is applied to said sample; and at least a first immobilized reagent disposed in said first liquid flow path for contacting said liquid biological sample as said sample flows from said sample chamber to said waste chamber;

wherein said first liquid flow path comprises a channel, and said non-frangible flow control means comprises at least a portion of said channel which constricts to prevent the flow of said liquid biological sample through said channel in the absence of a force applied to said sample, and which expands to permit said liquid biological sample to flow through said channel when at least said predetermined minimum force is applied to said sample.

2. A test unit as claimed in claim 1, wherein:

said waste chamber is spaced from said sample chamber; and said first liquid flow path extends in a non-reversing manner between said sample chamber and said waste chamber.

3. A test unit as claimed in claim 1 or 2, wherein said immobilized reagent comprises a nucleic acid probe.

4. A test unit as claimed in claim 3, further comprising a dried amplification reagent disposed in said sample chamber for carrying out nucleic acid amplification in said liquid biological sample.

5. A test unit as claimed in claim 1 or 2, wherein said sample chamber is provided with an opening for allowing said liquid biological sample to be introduced into said sample chamber, and further comprising a closure for sealing said opening after said liquid biological sample has been introduced.

6. A test unit as claimed in claim 1 or 2, further comprising:

at least one reagent chamber within said test unit in fluid communication with said first liquid flow path and said waste chamber for containing a liquid reagent; and a second liquid flow path for said liquid reagent within said test unit communicating from said reagent chamber to said first liquid flow path and said waste chamber.

7. A test unit as claimed in claim 6, wherein said second liquid flow path communicates directly with said first liquid flow path.

8. A test unit as claimed in claim 6, wherein said second liquid flow path communicates indirectly with said first liquid flow path through said sample chamber.

9. A test unit as claimed in claim 1, wherein said channel or portion thereof comprises opposed walls which are substantially in contact with each other in the absence of a force applied to said liquid biological sample, at least one of said walls having sufficient resiliency to allow said walls to be forced apart to permit said liquid biological sample to flow through said channel when at least said predetermined minimum force is applied to said sample.

10. An apparatus for performing a plurality of clinical diagnostic assays substantially simultaneously, said apparatus comprising:

a rotatable holder for carrying a plurality of test units and for rotating said test units about an axis;

a source of rotary power coupled to said rotatable holder for rotating said rotatable holder about said axis; and a plurality of test units carried by said rotatable holder and spaced circumferentially about said axis, each of said test units comprising a sample chamber within said test unit for receiving a liquid biological sample to be assayed, a waste chamber within said test unit in fluid communication with said sample chamber for receiving said liquid biological sample from said sample chamber, a first liquid flow path within said test unit communicating between said sample chamber and said waste chamber, and at least a first immobilized reagent disposed in said first liquid flow path, each of said disposable test units being oriented with respect to said rotatable holder in a manner such that said sample chamber is located closer to said axis than said waste chamber in order to cause said liquid biological sample to flow through said first liquid flow path from said sample chamber to said waste chamber and to thereby be brought into contact with said first immobilized reagent when at least a predetermined minimum centrifugal force is exerted on said liquid biological sample by rotation of said holder at a first rotational speed;

wherein said first liquid flow path in each of said test units comprises a channel, at least a portion of said channel being adapted to constrict to prevent the flow of said liquid biological sample through said channel in the absence of a force applied to said sample, and to expand to permit said liquid biological sample to flow through said channel when at least said predetermined minimum centrifugal force is applied to said sample by rotation of said holder at said first predetermined rotational speed.

11. An apparatus as claimed in claim 10, further comprising at least a first sensor operatively associated with said rotatable holder for detecting responses by said first immobilized reagents of said test units to the presence of a chemical or biological component in said liquid biological samples.

12. An apparatus as claimed in claim 11, wherein said first sensor is mounted at a fixed position on said apparatus with respect to said rotatable holder.

13. An apparatus as claimed in claim 12, wherein said source of rotary power is adapted to index said rotatable holder about said axis in order to allow said first sensor to detect said responses during stopped intervals of said rotatable holder.

14. An apparatus as claimed in claim 11, wherein each of said test units comprises a second immobilized reagent disposed in said first liquid flow path, said second immobilized reagent being different from said first immobilized reagent for responding to the presence of a different chemical or biological component in said liquid biological sample, and wherein said apparatus comprises at least a second sensor operatively associated with said rotatable holder for detecting responses by said second immobilized reagents.

15. An apparatus as claimed in claim 14, wherein said first and second immobilized reagents generate responses selected from the group consisting of chromogenic, fluorescent, chemiluminescent, bioluminescent and radioactive responses.

16. An apparatus as claimed in claim 10, further comprising at least a first heat source operatively associated with said rotatable holder for applying heat to the sample chambers of said test units.

17. An apparatus as claimed in claim 16, further comprising a second heat source operatively associated with said rotatable holder for applying heat to the first liquid flow paths and first immobilized reagents of said test units.

18. An apparatus as claimed in claim 17, wherein said first and second heat sources are disposed at fixed positions on said apparatus with respect to said rotatable holder.

19. An apparatus as claimed in claim 10, wherein each of said test units further comprises:
a reagent chamber within said test unit in fluid communication with said first liquid flow path and said waste chamber for containing a liquid reagent, said reagent chamber being located closer to said axis than said first liquid flow path when said test unit is carried by said rotatable holder; and
a second liquid flow path for said liquid reagent within said test unit communicating from said reagent chamber to said first liquid flow path and said waste chamber, said second liquid flow path including flow control means for preventing the flow of said liquid reagent therethrough at said first rotational speed and for permitting the flow of said liquid reagent therethrough at a second rotational speed higher than said first rotational speed;
and wherein said apparatus further comprises control means connected to said source of rotary power for selectively operating said source of rotary power at said first or second rotational speed.

20. An apparatus as claimed in claim 10, further comprising automated control means connected to said source of rotary power and to said sensor for effecting automatic control of said apparatus.

21. A test unit for carrying out a clinical diagnostic assay, comprising:
a sample chamber within said test unit for receiving a liquid biological sample to be assayed;
a waste chamber within said test unit in fluid communication with said sample chamber for receiving said liquid biological sample from said sample chamber;
a first liquid flow path for said liquid biological sample within said test unit communicating between said sample chamber and said waste chamber;
at least a first immobilized reagent disposed in said liquid flow path for contacting said liquid biological sample as said sample flows from said sample chamber to said waste chamber;
at least a first reagent chamber within said test unit in fluid communication with said first liquid flow path and said waste chamber for containing a first liquid reagent; and
a second liquid flow path for said first liquid reagent within said test unit communicating from said first reagent chamber to said first liquid flow path and said waste chamber;
wherein said sample chamber, said waste chamber and said first reagent chamber are disposed in an in-line arrangement within said test unit, with said waste chamber and said first reagent chamber disposed on opposite sides of said sample chamber, and
wherein at least one of said first and second liquid flow paths comprises a channel, at least a portion of said channel being adapted to constrict to prevent the flow of said liquid biological sample through said channel in the absence of a force applied to said sample, and to expand to permit said liquid biological sample to flow through said channel when at least a predetermined minimum force is applied to said sample.

22. A test unit as claimed in claim 21, wherein said second liquid flow path communicates directly with said first liquid flow path.

23. A test unit as claimed in claim 21, wherein said second liquid flow path communicates indirectly with said first liquid flow path through said sample chamber.

24. A test unit as claimed in claim 22 or 23, wherein said first and second liquid flow paths are non-reversing.

25. A test unit as claimed in claim 21, further comprising:
a second reagent chamber within said test unit in fluid communication with said first liquid flow path and said waste chamber for containing a second liquid reagent; and
a third liquid flow path for said second liquid reagent within said test unit communicating from said second reagent chamber to said first liquid flow path and said waste chamber;
wherein said second reagent chamber is disposed in an in-line arrangement with said sample chamber, said waste chamber and said first reagent chamber within said test unit, with said sample chamber and said second reagent chamber being disposed on opposite sides of said first reagent chamber.

26. A test unit as claimed in claim 25, further comprising:
a third reagent chamber within said test unit in fluid communication with said first liquid flow path and said waste chamber for containing a third liquid reagent; and
a fourth liquid flow path for said third liquid reagent within said test unit communicating from said third reagent chamber to said first liquid flow path and said waste chamber;
wherein said third reagent chamber is disposed in an in-line arrangement with said sample chamber, said waste chamber and said first and second reagent chambers within said test unit, with said first and third reagent chambers being disposed on opposite sides of said second reagent chamber.

27. A test unit as claimed in claim 21, wherein said immobilized reagent comprises a nucleic acid probe, said sample chamber contains a dried amplification reagent therein for carrying out nucleic acid amplification in said liquid biological sample, and said first reagent chamber is pre-filled with said first liquid reagent.

28. A test unit for carrying out a clinical diagnostic assay, comprising:

- a sample chamber within said test unit for receiving a liquid biological sample to be assayed;
- a waste chamber within said test unit in fluid communication with said sample chamber for receiving said liquid biological sample from said sample chamber;
- a first liquid flow path for said liquid biological sample within said test unit communicating between said sample chamber and said waste chamber; and
- at least a first immobilized reagent disposed in said first liquid flow path for contacting said liquid biological sample as said sample flows from said sample chamber to said waste chamber;
- wherein said sample chamber is provided in the form of a well having a liquid-receiving bottom portion and an upper portion communicating with said first liquid flow path, whereby a liquid biological sample only partially filling said sample chamber is unable to flow through said first liquid flow path to said immobilized reagent and said waste chamber in the absence of a force applied to said liquid biological sample which is sufficient to cause said sample to climb said well to reach said first liquid flow path; and
- wherein said first liquid flow path comprises a channel, at least a portion of said channel being adapted to constrict to prevent the flow of said liquid biological sample through said channel in the absence of a force applied to said sample, and to expand to permit said liquid biological sample to flow through said channel when at least a predetermined minimum force is applied to said sample.

29. A test unit as claimed in claim 28, further comprising:

- a plurality of reagent chambers within said test unit in fluid communication with said first liquid flow path and said waste chamber for containing a plurality of liquid reagents; and
- a corresponding plurality of additional liquid flow paths for said respective liquid reagents within said test unit communicating from said respective reagent chambers to said first liquid flow path and said waste chamber;
- each of said plurality of reagent chambers being provided in a form of a well having a liquid-receiving bottom portion and an upper portion communicating with a respective one of said additional liquid flow paths, whereby liquid reagents only partially filling said reagent chambers are unable to flow through said respective ones of said additional liquid flow paths to reach said immobilized reagent and said waste chamber in the absence of forces applied to said liquid reagents which are sufficient to cause said reagents to climb said wells to reach said respective ones of said additional liquid flow paths.

* * * * *